(12) United States Patent
Green et al.

(10) Patent No.: US 8,841,293 B1
(45) Date of Patent: Sep. 23, 2014

(54) TETRAHYDROPYRROLOTHIAZINE COMPOUNDS

(71) Applicant: Eli Lilly and Company, Indianapolis, IN (US)

(72) Inventors: Steven James Green, Indianapolis, IN (US); Dustin James Mergott, Zionville, IN (US); Brian Morgan Watson, Indianapolis, IN (US); Leonard Larry Winneroski, Jr., Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/195,897

(22) Filed: Mar. 4, 2014

Related U.S. Application Data

(60) Provisional application No. 61/776,819, filed on Mar. 12, 2013.

(51) Int. Cl.
*A61K 31/542* (2006.01)
*C07D 513/04* (2006.01)

(52) U.S. Cl.
USPC .................................... 514/224.2; 544/48

(58) Field of Classification Search
USPC .................................. 544/48; 514/224.2
See application file for complete search history.

(56) References Cited

U.S. PATENT DOCUMENTS

| | | | |
|---|---|---|---|
| 7,868,000 B2 | 1/2011 | Zhu et al. | |
| 8,158,620 B2 | 4/2012 | Suzuki et al. | |
| 8,173,642 B2 | 5/2012 | Kobayashi et al. | |
| 8,198,269 B2 | 6/2012 | Motoki et al. | |
| 8,278,441 B2 | 10/2012 | Mergott et al. | |
| 8,338,407 B2 | 12/2012 | Hall et al. | |
| 8,450,331 B2 | 5/2013 | Zhu et al. | |
| 2009/0209755 A1 | 8/2009 | Suzuki et al. | |
| 2010/0160290 A1 | 6/2010 | Kobayashi et al. | |
| 2010/0317850 A1 | 12/2010 | Suzuki et al. | |
| 2011/0190279 A1 | 8/2011 | Hori et al. | |
| 2012/0245155 A1 | 9/2012 | Yoshida et al. | |

FOREIGN PATENT DOCUMENTS

| WO | WO 2009131974 A1 * | 10/2009 |
|---|---|---|
| WO | 2012093148 A1 | 7/2012 |
| WO | 2012098213 A1 | 7/2012 |
| WO | 2012098461 A1 | 7/2012 |
| WO | 2012138590 A1 | 10/2012 |
| WO | 2012162334 A1 | 11/2012 |

OTHER PUBLICATIONS

Patrick C. May et al; Robust Central Reduction of Amyloid-beta in Humans with an Orally Available, Non-Peptidic Beta-Secretase Inhibitor, The Journal of Neuroscience, Nov. 16, 2011, 31(46), pp. 16507-16516.
International Search Report, Apr. 25, 2014, X19899, PCT/US2014/020070, Eli Lilly and Company.
Written Opinion of the International Searching Authority, PCT/US2014/020070, Eli Lilly and Company, Apr. 25, 2014.

* cited by examiner

*Primary Examiner* — Kahsay Habte
(74) *Attorney, Agent, or Firm* — Nelsen L. Lentz

(57) ABSTRACT

The present invention provides a compound of Formula I:

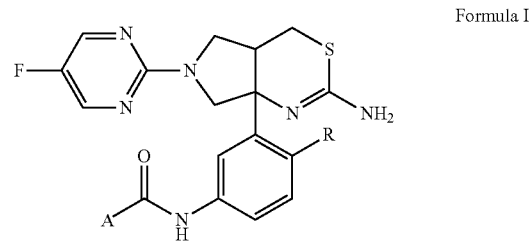

Formula I
wherein R is H or F; and
A is:

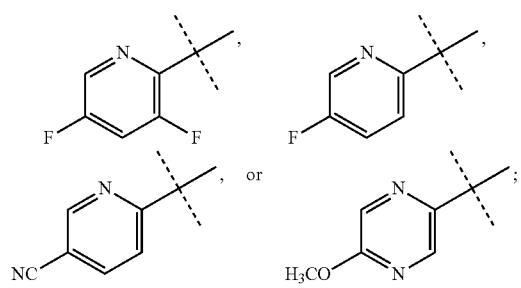

or a pharmaceutically acceptable salt thereof.

5 Claims, No Drawings

TETRAHYDROPYRROLOTHIAZINE COMPOUNDS

The present invention relates to novel tetrahydropyrrolothiazine compounds, to pharmaceutical compositions comprising the compounds, to methods of using the compounds to treat physiological disorders, and to intermediates and processes useful in the synthesis of the compounds.

The present invention is in the field of treatment of Alzheimer's disease and other diseases and disorders involving amyloid β (Abeta) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient, there is a significant unmet need in the treatment of Alzheimer's disease.

Alzheimer's disease is characterized by the generation, aggregation, and deposition of Abeta in the brain. Complete or partial inhibition of β-secretase (β-site amyloid precursor protein-cleaving enzyme; BACE) has been shown to have a significant effect on plaque-related and plaque-dependent pathologies in mouse models suggesting that even small reductions in Aβ peptide levels might result in a long-term significant reduction in plaque burden and synaptic deficits, thus providing significant therapeutic benefits, particularly in the treatment of Alzheimer's disease.

US 2009/0209755 discloses fused aminodihydrothiazine derivatives which possess BACE inhibitory activity and are further disclosed as useful therapeutic agents for a neurodegenerative disease caused by Aβ peptide, such as Alzheimer's type dementia. In addition, *J. Neuroscience,* 31(46), pages 16507-16516 (2011) discloses (S)-4-(2,4-difluoro-5-pyrimidin-5-yl-phenyl)-4-methyl-5,6-dihydro-4H-[1,3]thiazin-2-ylamine, an orally administered CNS-active BACE inhibitor.

BACE inhibitors that are potent with sufficient CNS penetration are desired to provide treatments for Abeta peptide-mediated disorders, such as Alzheimer's disease. The present invention provides certain novel compounds that are potent inhibitors of BACE. In addition, the present invention provides certain novel compounds with CNS penetration.

Accordingly, the present invention provides a compound of Formula I:

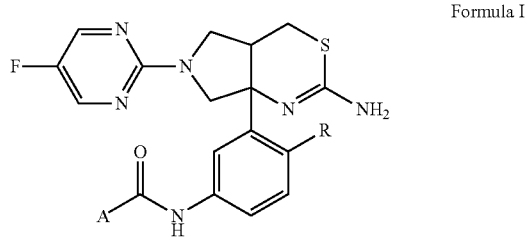

Formula I wherein R is H or F; and

A is:

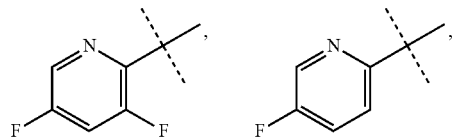

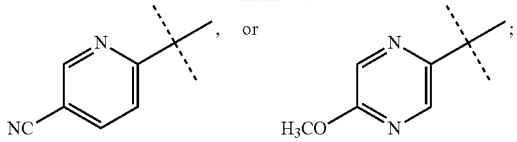

or a pharmaceutically acceptable salt thereof.

The present invention also provides a method of treating Alzheimer's disease in a patient, comprising administering to a patient in need of such treatment an effective amount of a compound of Formula I, or a pharmaceutically acceptable salt thereof.

The present invention further provides a method of preventing the progression of mild cognitive impairment to Alzheimer's disease in a patient, comprising administering to a patient in need of such treatment an effective amount of a compound of Formula I, or a pharmaceutically acceptable salt thereof.

The present invention also provides a method of inhibiting BACE in a patient, comprising administering to a patient in need of such treatment an effective amount of a compound of Formula I, or a pharmaceutically acceptable salt thereof.

The present invention also provides a method for inhibiting BACE-mediated cleavage of amyloid precursor protein, comprising administering to a patient in need of such treatment an effective amount of a compound of Formula I, or a pharmaceutically acceptable salt thereof.

The invention further provides a method for the inhibition of production of Abeta peptide, comprising administering to a patient in need of such treatment an effective amount of a compound of Formula I, or a pharmaceutically acceptable salt thereof.

Furthermore, this invention provides a compound of Formula I or a pharmaceutically acceptable salt thereof for use in therapy, in particular for the treatment of Alzheimer's disease or for the prevention of the progression of mild cognitive impairment to Alzheimer's disease. Even furthermore, this invention provides the use of a compound of Formula I, or a pharmaceutically acceptable salt thereof, for the manufacture of a medicament for the treatment of Alzheimer's disease. This invention also provides the use of a compound of Formula I, or a pharmaceutically acceptable salt thereof, for the manufacture of a medicament for the prevention of the progression of mild cognitive impairment to Alzheimer's disease. The invention also provides the use of a compound of Formula I, or a pharmaceutically acceptable salt thereof, for the manufacture of a medicament for the inhibition of BACE. The invention further provides the use of a compound of Formula I, or a pharmaceutically acceptable salt thereof, for the manufacture of a medicament for the inhibition of production of Abeta peptide.

The invention further provides a pharmaceutical composition, comprising a compound of Formula I, or a pharmaceutically acceptable salt thereof, in combination with one or more pharmaceutically acceptable carriers, diluents, or excipients. In a particular embodiment, the composition further comprises one or more other therapeutic agents. This invention also encompasses novel intermediates and processes for the synthesis of the compounds of Formula I.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.,* 58, 397-405 (2001); Petersen, et al., *Arch. Neurol.,* 56, 303-308 (1999)).

The term "prevention of the progression of mild cognitive impairment to Alzheimer's disease" includes slowing, arresting, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

The term "inhibition of production of Abeta peptide" is taken to mean decreasing of in vivo levels of Abeta peptide in a patient.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and parenteral routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

One of ordinary skill in the art will appreciate that compounds of the invention can exist in tautomeric forms, as depicted in Scheme A. When any reference in this application to one of the specific tautomers of the compounds of the invention is given, it is understood to encompass both tautomeric forms and all mixtures thereof.

Scheme A

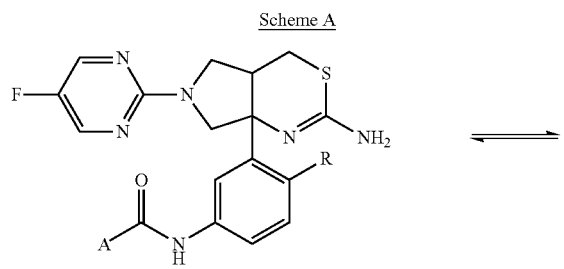

-continued

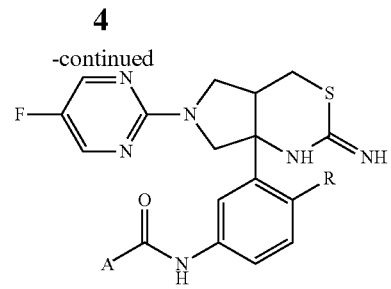

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formula I, or salts thereof. The products of each step in the schemes below can be recovered by conventional methods, including extraction, evaporation, precipitation, chromatography, filtration, trituration, and crystallization.

Certain stereochemical centers have been left unspecified and certain substituents have been eliminated in the following schemes for the sake of clarity and are not intended to limit the teaching of the schemes in any way. Furthermore, individual isomers, enantiomers, or diastereomers may be separated or resolved by one of ordinary skill in the art at any convenient point in the synthesis of compounds of Formula I by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples. Additionally, the intermediates described in the following schemes contain a number of nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

One of ordinary skill in the art will appreciate that compounds of the invention are comprised of a core that contains at least two chiral centers:

Scheme B

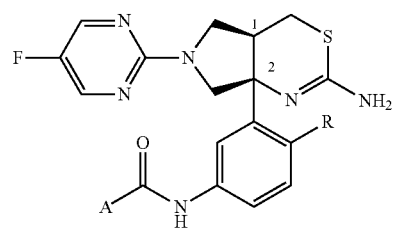

Although the present invention contemplates all individual enantiomers, as well as mixtures of the enantiomers of said compounds, including racemates, the compounds with the absolute configuration at the carbon atoms labeled 1 and 2 as illustrated in Scheme B are preferred compounds of the invention.

Abbreviations used herein are defined according to *Aldrichimica Acta*, Vol. 17, No. 1, 1984. Other abbreviations are defined as follows: "APP" refers to amyloid precursor protein; "BOC" refers to tert-butyloxycarbonyl; "CSF" refers to cerebrospinal fluid; "DCC" refers to 1,3-dicyclohexylcarbodiimide; "DIC" refers to diisopropylcarbodiimide; "DMEM" refers to Dulbecco's Modified Eagle's Medium; "DMSO" refers to dimethyl sulfoxide; "EDCI" refers to 1-(3-dimethylaminopropyl)-3-ethylcarbodiimide hydrochloride; "ee" refers to enantiomeric excess; "EtOAc" refers to ethyl acetate; "Ex" refers to example; "F12" refers to Ham's F12 medium; "FBS" refers to Fetal Bovine Serum; "FRET" refers to fluorescence resonance energy transfer; "HEK" refers to human embryonic kidney; "HOAc" refers to acetic acid; "HOAt" refers to 1-hydroxy-7-azobenzotriazole; "HOBt" refers to 1-hydroxylbenzotriazole hydrate; "HPLC" refers to high-performance liquid chromatography; "hr refers to hour or hours; "IC$_{50}$" refers to the concentration of an agent that produces 50% of the maximal inhibitory response possible for that agent; "min" refers to minute or minutes; "MTBE" refers to methyl tert-butyl ether; "PDAPP" refers to platelet derived amyloid precursor protein; "Prep" refers to preparation; "RFU" refers to relative fluorescence unit "R$_t$," refers to retention time; "RT" refers to room temperature; "SCX" refers to strong cation exchange; "SFC" refers to supercritical fluid chromatography; and "THF" refers to tetrahydrofuran.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

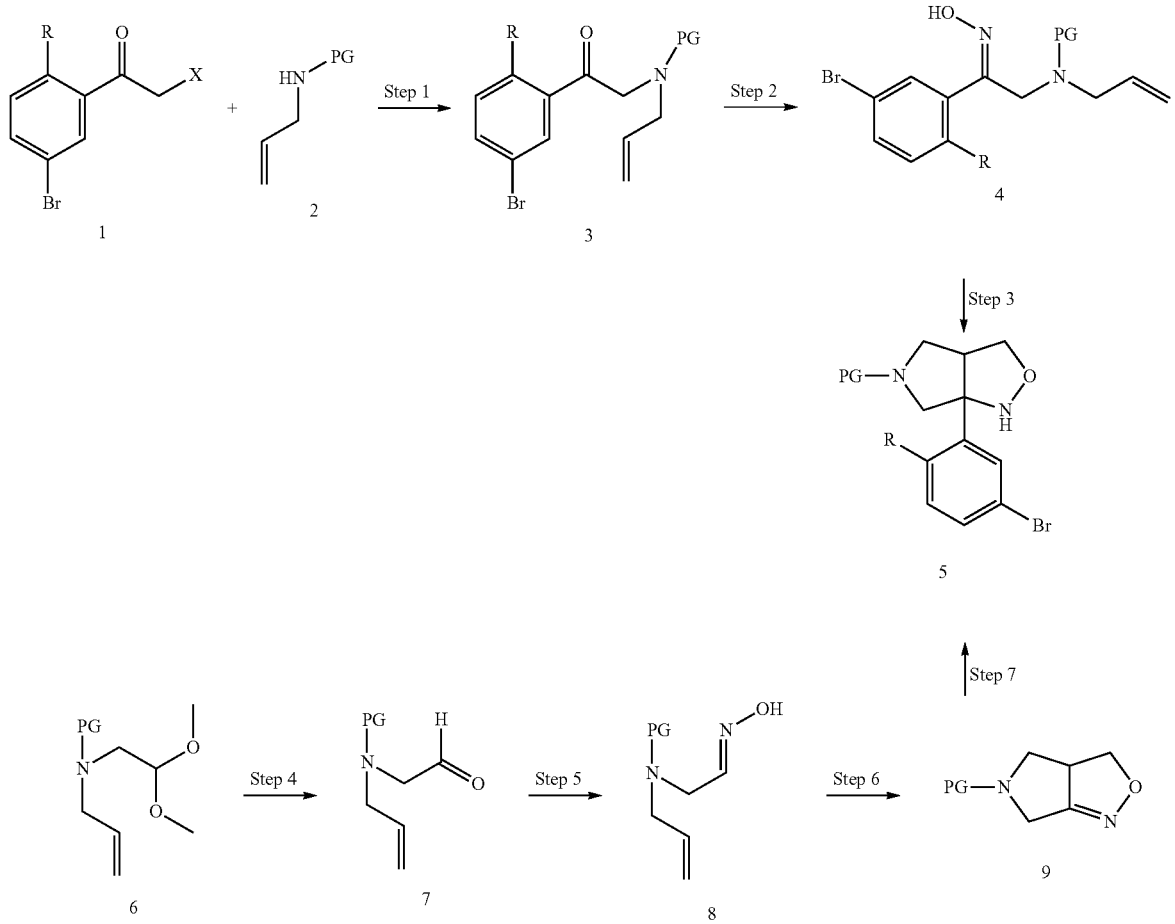

Scheme 1 depicts the formation of oximes (4) and (8). The oximes can each be used to form the bicyclic isoxazole (5). The substituted aromatic group can be inserted at different points of the synthesis as shown in Scheme 1, Step 1 and Step 7. "PG" is a protecting group developed for the amino group, such as carbamates and allyl. Such groups are well known and appreciated in the art.

In a 2-step reaction, a ketone with a beta halogen (1) can be alkylated (3, Step 1) with a protected allyl amine (2) using an inorganic base such as potassium carbonate and then treated with hydroxylamine hydrochloride and an organic base such as pyridine in a polar protic solvent such as ethanol to give the oxime (4, Step 2). The oxime (4) can then be converted to the bicyclic isoxazole (5) in a 3+2 cyclization by several methods such as heating the oxime (4) in a non-polar solvent such as toluene or xylenes to form the bicyclic isoxazole (5, Step 3). Alternatively, an oxime can be formed starting from a dimethyl acetal (6) which is treated with an acid such as formic acid to form the aldehyde (7, Step 4). In step 5, the aldehyde (7) can then be converted to the oxime (8) with hydroxylamine hydrochloride and a base such as sodium acetate trihydrate. The bicyclic isoxazole (9) can be formed from the oxime (8) as shown in Step 6 using an aqueous solution of sodium hypochlorite. In step 7, the protected bicyclic isoxazole (9) is then reacted with an aromatic organolithium reagent or Grignard reagent to give protected bicyclic isoxazole (5).

Scheme 3

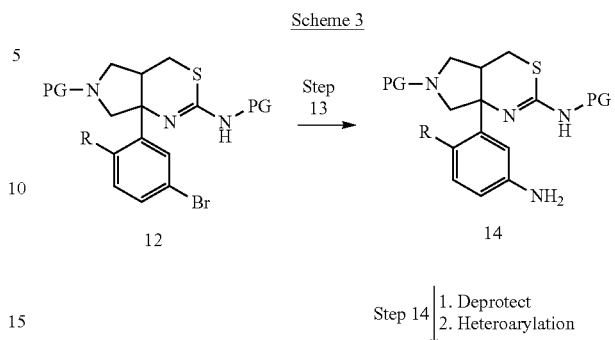

Scheme 2

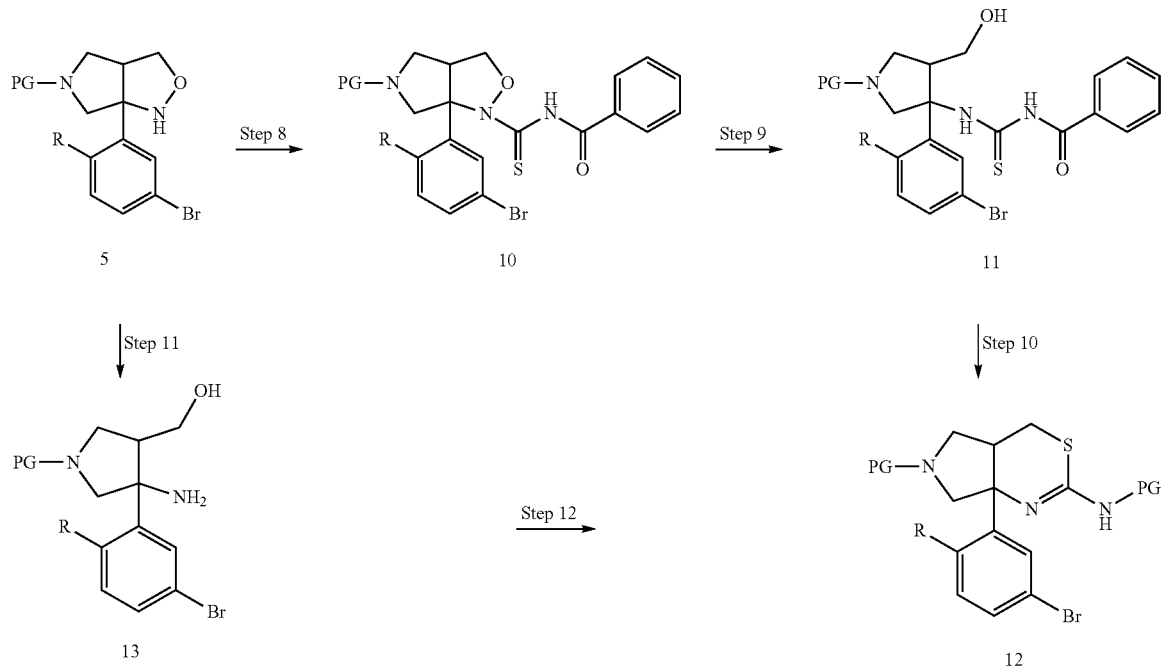

Scheme 2 illustrates different routes to the protected pyrrolo thiazine (12). The protected bicyclic isoxazole (5) can be treated with powdered Zn in acetic acid or by Raney Nickel in a polar solvent such as ethanol under pressure hydrogenation conditions to give an aminopyrrolidine methanol (13, Step 11). The aminopyrrolidine methanol (13) is then reacted with benzoyl isothiocyanate in a polar solvent such as THF followed by the addition of 1,1 carbonyldiimidazole (CDI) to give the fused protected pyrrolidine thiazine (12, Step 12). Alternatively, the amine of the bicyclic isoxazole (5) can be reacted with benzoyl isothiocyanate to give the thiourea (10, Step 8), and then, in Step 9 the isoxazole ring can be opened with powdered zinc in acetic acid to give the hydroxyl compound (11). The hydroxyl compound (11) can then be treated with CDI in a polar aprotic solvent such as THF or 1-chloro-N,N,2-trimethylpropenylamine in DCM to form the fused protected pyrrolidine thiazine (12, Step 10). The fused pyrrolidine thiazine (12) can also be formed from a Mitsunobu reaction such as using triphenylphosphine and diisopropyl azodicarboxylate (DIAD).

-continued

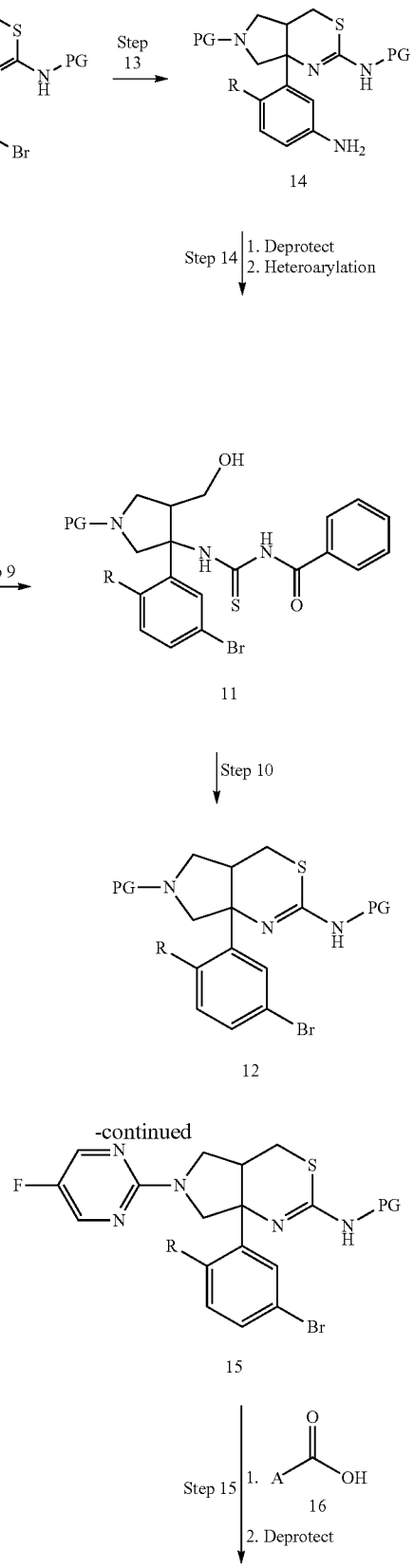

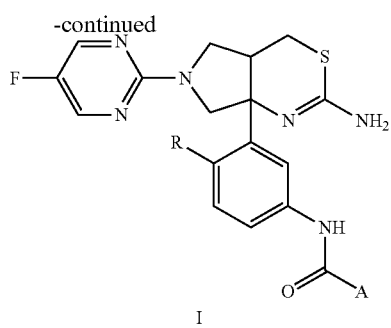

I

Scheme 3 depicts the conversion of the pyrrolo thiazine (12) to the aniline (14, Step 13) which can then be acylated followed by the deprotection and heteroarylation of the pyrrolidine. Deprotection of the thiazine amine leads to compounds of Formula I.

Azido-dehalogenation is performed on the appropriate pyrrolo thiazine (12) in the presence of an azide source, such as sodium azide. Such azido-dehalogenation reactions are well known and appreciated in the art. Reduction of the resulting azide intermediate to the aniline (14, Step 13) may be effected by hydrogenation conditions that are well known and described in the art or by reducing agents well known in the art, such as $LiAlH_4$, $NaBH_4$, $PPh_3$.

A BOC protected pyrrolidine can be deprotected under acidic conditions well known in the art (Step 1 of Step 14). The deprotected pyrrolidine can then be heteroarylated in a nucleophilic aromatic substitution (SNAr) with a substituted aromatic pyrimidine using an organic base such as diisopropylethylamine, triethylamine, or N,N,N,N'-tetramethylguanidine to give compound 15 (Step 2 of Step 14). The aniline (15) can be coupled with heteroaromatic carboxylic acids (16) under coupling conditions (Step 1 of Step 15). One skilled in the art will recognize that there are a number of methods and reagents for amide formation resulting from the reaction of carboxylic acids and amines. For example, the reaction of an appropriate aniline (15) with an appropriate acid of compound 16 in the presence of a coupling reagent and an amine base such as DIPEA or triethylamine, will give a compound of Formula I following deprotection of the thiazine amine. Coupling reagents include carbodiimides such as DCC, DIC, EDCI, and aromatic oximes such as HOBt and HOAt. Additionally, uronium or phosphonium salts of non-nucleophilic anions such as HBTU, HATU, PyBOP, and PyBrOP can be used in place of the more traditional coupling reagents. Additives such as DMAP may be used to enhance the reaction. Alternatively, the protected aniline amine (15) can be acylated using substituted benzoyl chlorides in the presence of a base such as triethylamine or pyridine. The protected thiazine amine can then be deprotected with an organic base such as pyridine and methylhydroxylamine hydrochloride in a polar aprotic solvent such as ethanol or an inorganic base such as lithium hydroxide in methanol to give compounds of Formula I.

In an optional step, a pharmaceutically acceptable salt of a compound of Formula I can be formed by reaction of an appropriate free base of Formula I with an appropriate pharmaceutically acceptable acid in a suitable solvent under standard conditions. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). One of ordinary skill in the art will appreciate that a compound of Formula I is readily converted to and may be isolated as a pharmaceutically acceptable salt, such as a hydrochloride salt.

PREPARATIONS AND EXAMPLES

The following preparations and examples further illustrate the invention. Unless noted to the contrary, the compounds illustrated herein are named and numbered using Symyx® Draw version 3.2 or version 4.0 (Symyx Solutions, Inc.) or IUPACNAME ACDLABS.

Preparation 1

1-(3-Bromophenyl)-2-(diallylamino)ethanone

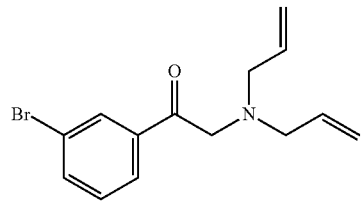 [SMILES: C=CCN(CC=C)CC(=O)c1cccc(Br)c1]

Potassium carbonate (38.8 g, 281 mmol) is added to 3-bromophenacyl bromide (60 g 216 mmol) in acetonitrile (430 mL), and the mixture is cooled under nitrogen to 0° C. Diallylamine (34.6 mL, 280.63 mmol) is added drop wise over 1 hour and the reaction is allowed to warm to 22° C. overnight. The crude reaction mixture is concentrated and the residue is partitioned in water (300 mL) and MTBE (300 mL). The aqueous layer is discarded and the organic layer is washed with water (100 mL, 2×) and with brine (100 mL). The organic layer is dried over sodium sulfate, filtered, and the solvent evaporated to constant weight to give the title compound (62 g, 98%). ES/MS (m/e): 294 (M+1).

Preparation 2

Benzyl N-(2,2-dimethoxyethyl)carbamate

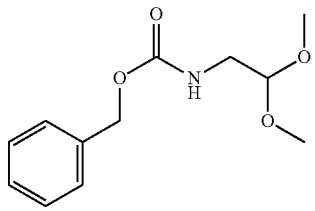 [SMILES: COC(CNC(=O)OCc1ccccc1)OC]

A solution of aminoacetaldehyde dimethyl acetal (25 mL, 229 mmol) in toluene (120 mL) is treated at 0° C. with a 4.85 M sodium hydroxide solution (70.8 mL, 343.5 mmol). The mixture is stirred at 0° C. for 10 minutes and benzyl chloroformate (33.8 mL, 229 mmol) is added keeping the internal temperature below 20° C. during the addition. The mixture is warmed to room temperature over 4 hours. The organic layer is separated, washed with brine, dried over sodium sulfate, and concentrated to dryness to give the title compound (54 g, 98%). ES/MS (m/e): 240 (M+H).

Preparation 3

Benzyl N-allyl-N-(2,2-dimethoxyethyl)carbamate

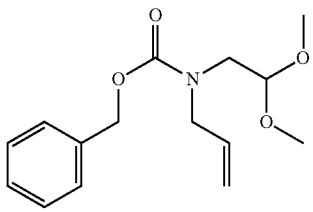 [SMILES: C=CCN(CC(OC)OC)C(=O)OCc1ccccc1]

A solution of benzyl N-(2,2-dimethoxyethyl)carbamate (50 g, 208.9 mmol) in toluene (180 mL) is treated with solid potassium hydroxide (51.6 g, 919.69 mmol) under nitrogen. After 10 minutes, benzyltriethylammonium chloride (0.8 g, 3.1 mmol) is added. After another 10 minutes a solution of allyl bromide (33 g, 272.8 mmol) in toluene (50 mL) is added drop wise over 10 minutes. The resultant mixture is stirred at 50° C. for 48 hours. The mixture is cooled to room temperature and quenched with water. The organic layer is separated, washed with brine, dried over magnesium sulfate, and concentrated to dryness to give the title compound (44 g, 75%). ES/MS (m/e): 280 (M+H).

Preparation 4

Benzyl N-allyl-N-(2-oxoethyl)carbamate

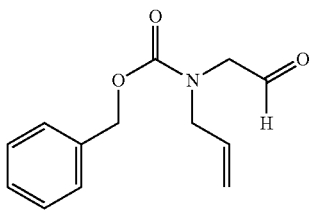 [SMILES: C=CCN(CC=O)C(=O)OCc1ccccc1]

A solution of benzyl N-allyl-N-(2,2-dimethoxyethyl)carbamate (30 g, 107 mmol) in formic acid (36.8 mL, 860 mmol) and water (4.84 mL) is stirred at room temperature overnight. The mixture is concentrated and diluted with hexanes/ethyl acetate (1:2) and water. The organic layer is separated, washed with brine solution until pH=6, and dried over sodium sulfate. The solvent is evaporated to give the title compound (25 g, 99%). ES/MS (m/e): 234 (M+H).

Preparation 5

1-(3-Bromophenyl)-2-(diallylamino)ethanone oxime

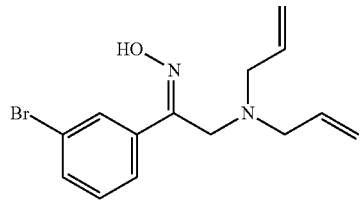 [SMILES: C=CCN(CC=C)C/C(=N/O)c1cccc(Br)c1]

A solution of 1-(3-bromophenyl)-2-(diallylamino)ethanone (60 g, 204.7 mmol) in ethanol (720 mL) and pyridine (24.8 mL, 307 mmol) is stirred 15 minutes at 22° C. Hydroxylamine hydrochloride (17 g, 246 mmol) is added in portions to the solution over 1 hour. The reaction is warmed to 50° C. for 2 hours and then heated to 70° C. for 16 hours. The solvent is evaporated and the residue partitioned in water (300 mL) and methyl tert-butyl ether (300 mL). The organic layer is separated and washed with water (100 mL, 2×) and brine (100 mL). The organic layer is dried over sodium sulfate, filtered, and evaporated to dryness to give the title compound (75.5 g, 79%). ES/MS (m/e): 309 (M+1).

Preparation 6

Benzyl N-allyl-N-[2-hydroxyiminoethyl]carbamate

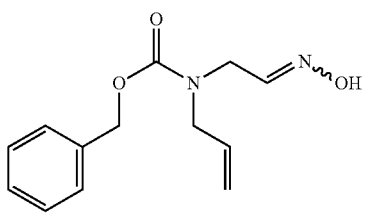 [SMILES: C=CCN(CC=NO)C(=O)OCc1ccccc1]

A solution of benzyl N-allyl-N-(2-oxoethyl)carbamate (25 g, 107 mmol) in acetonitrile (150 mL) is treated with hydroxylamine hydrochloride (9.68 g, 139 mmol) and a solution of sodium acetate trihydrate (16 g, 117.9 mmol) in water (75 mL). The mixture is stirred at room temperature overnight. The acetonitrile is evaporated and the aqueous solution is extracted with ethyl acetate. The organic layer is separated, dried over magnesium sulfate, and concentrated under vacuum to give the title compound (24 g, 90%). ES/MS (m/e): 249 (M+H).

Preparation 7

5-Allyl-6a-(3-bromophenyl)-3,3a,4,6-tetrahydro-1H-pyrrolo[3,4-c]isoxazole

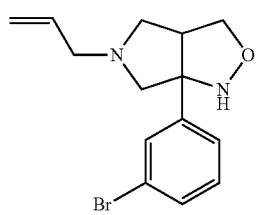 [SMILES: C=CCN1CC2CONC2(c2cccc(Br)c2)C1]

The crude 1-(3-bromophenyl)-2-(diallylamino)ethanone oxime (75.5 g, 195.34 mmol) is dissolved in toluene (600 mL) and refluxed for 12 hours. The solvent is evaporated in vacuo and the residue dissolved in a mixture of aqueous 1 N HCl (1 L) and methyl tert-butyl ether (300 mL). The mixture is stirred for 15 minutes and diatomaceous earth (10 g) is added. The mixture is stirred for an additional 20 minutes and filtered through diatomaceous earth. The filter cake is washed with additional aqueous 1 N HCl (200 mL) and methyl tert-butyl ether (200 mL). The organic layer is separated and washed with 1 N HCl (2×100 mL). The aqueous layers are combined and the pH adjusted to 9 with NaOH 50% w/w. The aqueous mixture is extracted with methyl tert-butyl ether (3×250 mL). The organic layers are combined, dried over sodium sulfate and filtered. The filtrate is evaporated and dried under vacuum to give a red solid (60 g). The red solid is diluted with heptane (600 mL) and the mixture heated to reflux for 20 minutes. Charcoal (2 g) is added and the mixture is filtered through diatomaceous earth. The filtrates are concentrated under atmospheric pressure to adjust the final volume to 300 mL. The solution is cooled to 22° C. and stirred for 3 hours. A pale yellow solid is collected by filtration and dried under vacuum to a constant weight to give the title compound (40 g, 60%). ES/MS (m/e): 309 (M+1).

Preparation 8

Benzyl 3,3a,4,6-tetrahydropyrrolo[3,4-c]isoxazole-5-carboxylate

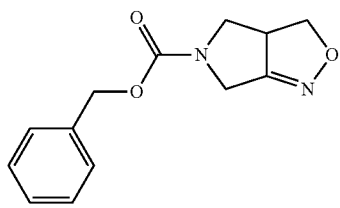 [SMILES: O=C(OCc1ccccc1)N1CC2=NOCC2C1]

A solution of Benzyl N-allyl-N-[2-hydroxyiminoethyl]carbamate (24 g, 96.6 mmol) in dichloromethane (338 mL) is treated drop wise over 10 minutes with a 5% w/w aqueous solution of sodium hypochlorite (106.08 mmol, 143.06 mL). The resultant mixture is stirred at room temperature overnight. The reaction is quenched with a 40% aqueous solution of sodium bisulfite (7 g). The organic layer is separated, dried over magnesium sulfate, and concentrated under vacuum. The crude product is purified over silica gel eluting with 5% ethyl acetate in hexanes to give the title compound (18 g, 75%). ES/MS (m/e): 247 (M+H).

Preparation 9

Benzyl 6a-(5-bromo-2-fluoro-phenyl)-3,3a,4,6-tetrahydro-1H-pyrrolo[3,4-c]isoxazole-5-carboxylate

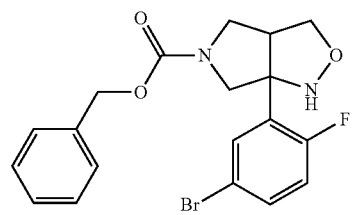 [SMILES: O=C(OCc1ccccc1)N1CC2CONC2(c2cc(Br)ccc2F)C1]

A 1.6 M hexanes solution of n-butyl lithium (25.4 mL, 40.6 mmol) is added drop wise to a −78° C. solution of 4-bromo-1-fluoro-2-iodobenzene (12.22 g, 40.6 mmol) in tetrahydrofuran (60 mL) to give a yellow solution that is stirred at −78° C. for 15 minutes. Boron trifluoride etherate (5.14 mL, 40.6 mmol) is added to a separate −78° C. solution of benzyl 3,3a,4,6-tetrahydropyrrolo[3,4-c]isoxazole-5-carboxylate (5 g, 20.3 mmol) in tetrahydrofuran (60 mL) and the mixture is stirred at −78° C. for 5 minutes. This solution is added to the previously prepared −78° C. organolithium mixture via cannula. The combined mixture is stirred for 30 minutes at −78° C. The mixture is quenched with saturated aqueous ammonium chloride and warmed to room temperature. The mixture is extracted with ethyl acetate (3×) and the organic extracts are combined, dried over sodium sulfate, filtered and the solvent removed in vacuo. The crude product is purified over silica gel with a 35 minute 5% to 100% ethyl acetate in hexanes gradient to give the title compound (2.27 g, 27%). ES/MS (m/e): ($^{79}$Br/$^{81}$Br) 421/423 (M+H).

Preparation 10

Benzyl 1-(benzoylcarbamothioyl)-6a-(5-bromo-2-fluoro-phenyl)-3,3a,4,6-tetrahydropyrrolo[3,4-c]isoxazole-5-carboxylate

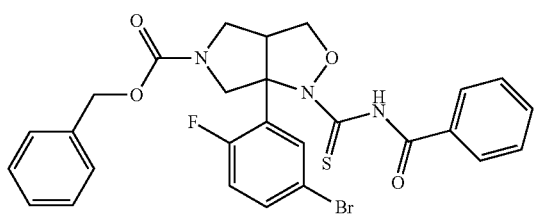 [SMILES: O=C(NC(=S)N1OCC2CN(C(=O)OCc3ccccc3)CC21c1cc(Br)ccc1F)c1ccccc1]

Benzoyl isothiocyanate (2.87 mL, 21.28 mmol) is added drop wise to a solution of benzyl 6a-(5-bromo-2-fluoro-phenyl)-3,3a,4,6-tetrahydro-1H-pyrrolo[3,4-c]isoxazole-5-carboxylate (5.977 g, 14.2 mmol) in tetrahydrofuran (95 mL) and stirred overnight under nitrogen. The solvent is removed in vacuo. The crude product is purified over silica gel with a 30 minute 5% to 100% EtOAc in hexanes gradient to give the title compound (6.05 g, 73%). ES/MS (m/e): ($^{79}$Br/$^{81}$Br) 584/586 (M+H).

Preparation 11

[1-Allyl-4-amino-4-(3-bromophenyl)pyrrolidin-3-yl]methanol

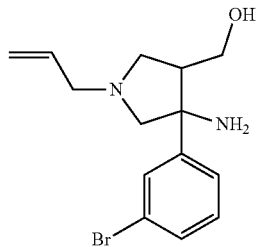 [SMILES: C=CCN1CC(CO)C(N)(c2cccc(Br)c2)C1]

A 22° C. solution of 5-allyl-6a-(3-bromophenyl)-3,3a,4,6-tetrahydro-1H-pyrrolo[3,4-c]isoxazole (40 g, 129.4 mmol) in acetic acid (400 mL) is treated with zinc dust (42.3 g, 646.8 mmol) in one portion. The reaction is stirred vigorously at room temperature for 1 hour. Ethyl acetate (400 mL) is added and the mixture is filtered through diatomaceous earth. The filtrate is evaporated and the residue dried under vacuum. The residue is partitioned in water (300 mL) and MTBE (300 mL). The pH is adjusted to 8 with sodium hydroxide 50% w/w and the organic layer is separated, dried over sodium sulfate, and filtered. The filtrate is evaporated and the residue dried under vacuum to give the title compound (41 g, 97%). ES/MS (m/e): 311 (M+1).

Preparation 12

Benzyl 3-(benzoylcarbamothioylamino)-3-(5-bromo-2-fluoro-phenyl)-4-(hydroxymethyl)pyrrolidine-1-carboxylate

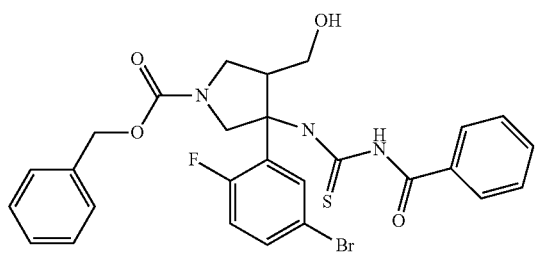 [SMILES: O=C(NC(=S)NC1(c2cc(Br)ccc2F)CN(C(=O)OCc2ccccc2)CC1CO)c1ccccc1]

A mixture of benzyl 1-(benzoylcarbamothioyl)-6a-(5-bromo-2-fluoro-phenyl)-3,3a,4,6-tetrahydropyrrolo[3,4-c]isoxazole-5-carboxylate (6.05 g 10.4 mmol) and zinc (dust, <10 micron) (6.77 g, 103.5 mmol) is stirred in acetic acid (52 mL) at room temperature overnight under nitrogen. The reaction is diluted with ethyl acetate and filtered through diatomaceous earth. The solvent is removed in vacuo and the residue is diluted with ethyl acetate, water and saturated aqueous sodium bicarbonate. The mixture is extracted with ethyl acetate (3×), the combined organic layers are combined and dried over sodium sulfate, filtered and the solvent removed in vacuo. The crude product is purified over silica gel with a 30 minute 5% to 100% EtOAc in hexanes gradient to give the title compound (5.222 g, 86%). ES/MS (m/e): ($^{79}$Br/$^{81}$Br) 586/588 (M+H).

Preparation 13

[(3R,4S)-1-Allyl-4-amino-4-(3-bromophenyl)pyrrolidin-3-yl]methanol; (2R,3R)-2,3-bis[(4-methylbenzoyl)oxy]butanedioic acid

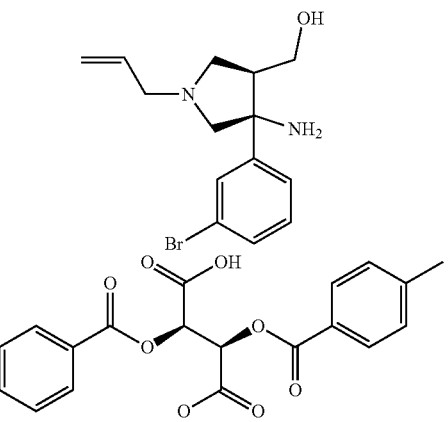

A solution of [1-allyl-4-amino-4-(3-bromophenyl)pyrrolidin-3-yl]methanol (77 g, 235 mmol) in isopropyl alcohol (914 mL) is heated to 70° C. Di-p-toluoyl-L-tartaric acid (86.2 g, 223 mmol) is added and the mixture is cooled to 22° C. over 2 hours and stirred overnight. The slurry is filtered to collect a pale yellow solid and washed with isopropyl alcohol. The solid is dried under vacuum to give the title compound (63 g, 36%). ES/MS (m/e): 311 (M+1). The product is analyzed by reverse phase chiral chromatography: Analysis of the first eluting isomer (Column: Chiralpak ID-3 4.6×50 mm; eluent: 70:30, aqueous 20 mM ammonium bicarbonate: acetonitrile; flow: 1.5 mL/min at UV 215 nm) confirms the enantiomerically enriched (96% ee) enantiomer with $R_t$=1.26 minutes.

Preparation 14

[(3R,4S)-1-Allyl-4-amino-4-(3-bromophenyl)pyrrolidin-3-yl]methanol

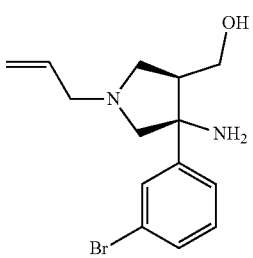 [SMILES: C=CCN1C[C@@H](CO)[C@](N)(c2cccc(Br)c2)C1]

[(3R,4S)-1-Allyl-4-amino-4-(3-bromophenyl)pyrrolidin-3-yl]methanol; (2R,3R)-2,3-bis[(4-methylbenzoyl)oxy]butanedioic acid (63 g 85.8 mmol) is combined with aqueous 1 N HCl (800 mL) and ethyl acetate (400 mL) and the mixture is stirred for 15 minutes at 22° C. The layers are separated and the pH of the aqueous layer is adjusted to 10 with sodium hydroxide 50% w/w. The aqueous mixture is extracted with methyl tert-butyl ether (3×250 mL). The combined organic layers are dried over magnesium sulfate, filtered and evaporated to dryness to give the title compound (27 g, 99%). ES/MS (m/e): 311 (M+1).

Preparation 15

N-[(4aR,7aS)-6-Allyl-7a-(3-bromophenyl)-4,4a,5,7-tetrahydropyrrolo[3,4-d][1,3]thiazin-2-yl]benzamide

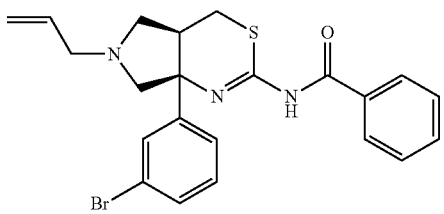 [SMILES: C=CCN1C[C@H]2CSC(NC(=O)c3ccccc3)=N[C@@]2(c2cccc(Br)c2)C1]

A solution of [(3R,4S)-1-allyl-4-amino-4-(3-bromophenyl)pyrrolidin-3-yl]methanol (27 g; 86.7 mmol) in tetrahydrofuran (270 mL) is cooled to −5° C. under a nitrogen atmosphere. Benzoyl isothiocyanate (12.3 mL, 91 mmol) is added drop wise keeping the temperature below 0° C. The reaction is allowed to warm to 22° C. over 1 hour. 1,1'-Carbonyldiimidazole (28.1 g, 173.5 mmol) is added in a single portion and the reaction is stirred for 1 hour at 22° C. and then heated to reflux for 16 hours. The solvent is removed in vacuo and the residue dried under vacuum. The crude material is partitioned in methyl tert-butyl ether (500 mL) and water (250 mL). The organic layer is separated, dried over magnesium sulfate, filtered and evaporated to dryness. The crude material is purified over a silica gel gradient of 90/10 to 60/40 methylene chloride/ethyl acetate to give the title compound (27 g, 68%). ES/MS (m/e): 456 (M+1).

Preparation 16

Benzyl 2-benzamido-7a-(5-bromo-2-fluoro-phenyl)-4,4a,5,7-tetrahydropyrrolo[3,4-d][1,3]thiazine-6-carboxylate

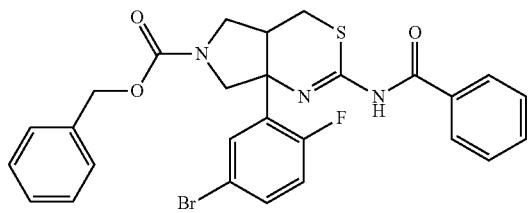 [SMILES: O=C(NC1=NC2(c3cc(Br)ccc3F)CN(C(=O)OCc3ccccc3)CC2CS1)c1ccccc1]

1,1'-carbonyldiimidazole (2.87 g, 17.7 mmol) is added to a solution of benzyl 3-(benzoylcarbamothioylamino)-3-(5-bromo-2-fluoro-phenyl)-4-(hydroxymethyl)pyrrolidine-1-carboxylate (5.198 g, 8.86 mmol) in tetrahydrofuran (52 mL). The mixture is stirred for 1.5 hours at room temperature and then the reaction is heated at reflux overnight under nitrogen. The reaction is cooled, diluted with water, and extracted with ethyl acetate (3×). The organic layers are combined, dried over sodium sulfate, filtered, and the solvent removed in vacuo. The crude product is purified over silica gel with a 30 minute 5% to 100% EtOAc in hexanes gradient to give the title compound (2.93 g, 58%). ES/MS (m/e): ($^{79}$Br/$^{81}$Br). 568/570 (M+H)

Preparation 17

N-[(4aR,7aS)-7a-(3-Bromophenyl)-4,5,6,7-tetrahydro-4H-pyrrolo[3,4-d][1,3]thiazin-2-yl]benzamide

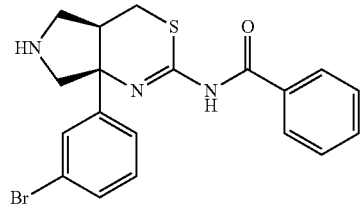 [SMILES: O=C(NC1=N[C@@]2(c3cccc(Br)c3)CNC[C@H]2CS1)c1ccccc1]

A room temperature mixture of N-[(4aR,7aS)-6-allyl-7a-(3-bromophenyl)-4,4a,5,7-tetrahydropyrrolo[3,4-d][1,3]thiazin-2-yl]benzamide (1 g, 2.19 mmol) and N,N-dimethylbarbituric acid (0.868 g, 5.48 mmol) in chloroform (22 mL) is degassed by bubbling nitrogen through the resulting slurry at RT for 5 min. The mixture is treated with tetrakis(triphenylphosphine)palladium (0.261 g, 219 μmoles) and is stirred for 1.5 hours under nitrogen.

In a separate flask, a mixture of N-[(4aR,7aS)-6-allyl-7a-(3-bromophenyl)-4,4a,5,7-tetrahydropyrrolo[3,4-d][1,3]thiazin-2-yl]benzamide (22.2 g, 48.6 mmol) and N,N-dimethylbarbituric acid (19.28 g, 121.6 mmol) in chloroform (486 mL) is degassed by bubbling nitrogen through the resulting slurry at RT for 5 min. The mixture is treated with tetrakis(triphenylphosphine)palladium (5.79 g, 4.86 mmol) and is stirred for 2 hours under nitrogen.

The two reactions are combined and the solvent is removed in vacuo to give the crude product. The crude material is purified over silica gel with a 30 minute 0.5% to 10% methanol in dichloromethane gradient to give the title compound (22.4 g, 100%). ES/MS (m/e): ($^{79}$Br/$^{81}$Br) 416/418 (M+H).

Preparation 18

N-[7a-(5-Bromo-2-fluoro-phenyl)-4a,5,6,7-tetrahydro-4H-pyrrolo[3,4-d][1,3]thiazin-2-yl]benzamide

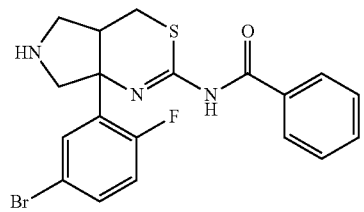 [SMILES: O=C(NC1=NC2(c3cc(Br)ccc3F)CNCC2CS1)c1ccccc1]

Iodotrimethylsilane (2.21 mL, 15.46 mmol) is added drop wise to a room temperature solution of benzyl 2-benzamido-7a-(5-bromo-2-fluoro-phenyl)-4,4a,5,7-tetrahydropyrrolo[3,4-d][1,3]thiazine-6-carboxylate (2.93 g, 5.15 mmol) in acetonitrile (44 mL). The reaction is stirred at room temperature for two hours and the solvent is removed in vacuo. The crude product is purified with an SCX column using 3:1 dichloromethane:methanol and then 2:1 dichloromethane:7 N ammonia in methanol to give the title compound (2.098 g, 94%). ES/MS (m/e): ($^{79}$Br/$^{81}$Br) 434/436 (M+H).

Preparation 19 tert-Butyl (4aR,7aS)-2-benzamido-7a-(3-bromophenyl)-4,4a,5,7-tetrahydropyrrolo[3,4-d][1,3]thiazine-6-carboxylate

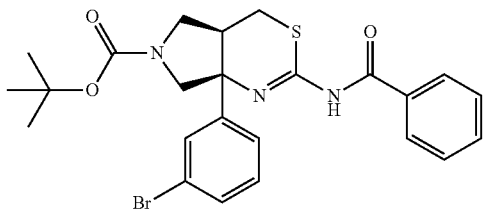 [SMILES: CC(C)(C)OC(=O)N1C[C@H]2CSC(NC(=O)c3ccccc3)=N[C@@]2(c2cccc(Br)c2)C1]

A room temperature solution of N-[(4aR,7aS)-7a-(3-bromophenyl)-4a,5,6,7-tetrahydro-4H-pyrrolo[3,4-d][1,3]thiazin-2-yl]benzamide (22.4 g, 36.69 mmol) in dichloromethane (367 mL) is treated with di-t-butyldicarbonate (8.81 g, 40.36 mmol) followed by triethylamine (7.67 mL, 55.04 mmol) and the reaction is stirred at room temperature for 1 hour under nitrogen. The solvent is removed in vacuo and the crude product is purified over silica gel with a 25 minute 5% to 100% ethyl acetate in hexanes gradient to give the title compound (20.22 g, 100%). ES/MS (m/e): ($^{79}$Br/$^{81}$Br) 516/518 (M+H).

Preparation 20 tert-Butyl 2-benzamido-7a-(5-bromo-2-fluoro-phenyl)-4,4a,5,7-tetrahydropyrrolo[3,4-d][1,3]thiazine-6-carboxylate

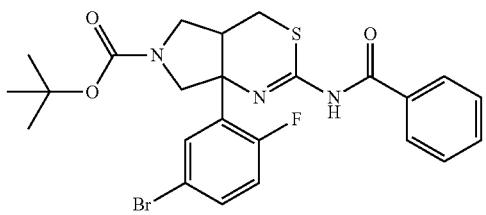 [SMILES: CC(C)(C)OC(=O)N1CC2CSC(NC(=O)c3ccccc3)=NC2(c2cc(Br)ccc2F)C1]

Di-t-butyldicarbonate (1.16 g, 5.31 mmol) and triethylamine (1.01 mL, 7.25 mmol) are added to a solution of N-[7a-(5-bromo-2-fluoro-phenyl)-4a,5,6,7-tetrahydro-4H-pyrrolo[3,4-d][1,3]thiazin-2-yl]benzamide (2.098 g, 4.83 mmol) in dichloromethane (48 mL). The reaction is stirred for 1 hour at room temperature under nitrogen. The solvent is removed in vacuo and the crude product is purified over silica gel with a 30 minute 5% to 100% EtOAc in hexanes gradient to give the title compound (2.556 g, 99%). ES/MS (m/e): ($^{79}$Br/$^{81}$Br) 534/536 (M+H).

Preparation 21 tert-Butyl (4aR,7aS)-7a-(3-aminophenyl)-2-benzamido-4,4a,5,7-tetrahydropyrrolo[3,4-d][1,3]thiazine-6-carboxylate

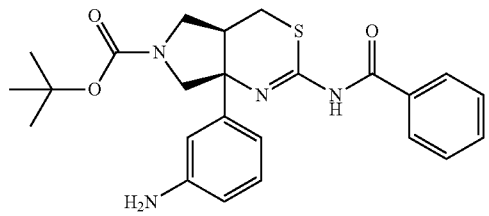 [SMILES: CC(C)(C)OC(=O)N1C[C@H]2CSC(NC(=O)c3ccccc3)=N[C@@]2(c2cccc(N)c2)C1]

A solution of tert-butyl (4aR,7aS)-2-benzamido-7a-(3-bromophenyl)-4,4a,5,7-tetrahydropyrrolo[3,4-d][1,3]thiazine-6-carboxylate (5 g, 9.7 mmol) and trans-N,N'-dimethyl-1,2-cyclohexanediamine (220.3 mg, 1.5 mmol) in ethanol (100 mL) is treated with sodium azide (1.30 g, 19.4 mmol). An aqueous solution of L-ascorbic acid sodium salt (0.66 M, 3.2 mL, 2.1 mmol) and water (10 mL) is added and the top of the flask is purged with nitrogen. The mixture is treated with an aqueous solution of copper(II)sulfate pentahydrate (0.33 M, 3.2 mL, 1.1 mmol) and the mixture is immediately heated on a preheated hot plate at 80° C. for 1.5 hrs under nitrogen. A homogeneous mixture is obtained upon heating. The reaction is cooled and ice water is added. The mixture is extracted with ethyl acetate (3×). The organic layers are combined and dried over sodium sulfate, filtered, and the solvent is removed in vacuo to give crude azide product. The crude azide product is combined with 10% palladium on carbon (2 g) in cold ethanol (150 mL) and the mixture is purged using vacuum/nitrogen and then vacuum/hydrogen. The mixture is stirred at room temperature under 30 psi of hydrogen for 2 hours. The reaction is vented and the mixture is filtered through diatomaceous earth using dichloromethane to rinse the filter cake. The solvent is removed from the filtrate in vacuo and the crude product is purified over silica gel with 50% ethyl acetate in dichloromethane to give the title compound (4 g, 91%). ES/MS (m/e): 453 (M+H).

Preparation 22 tert-Butyl 7a-(5-amino-2-fluoro-phenyl)-2-benzamido-4,4a,5,7-tetrahydropyrrolo[3,4-d][1,3]thiazine-6-carboxylate

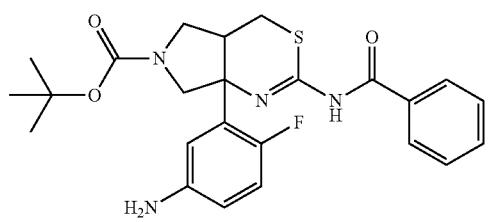 [SMILES: CC(C)(C)OC(=O)N1CC2CSC(NC(=O)c3ccccc3)=NC2(c2cc(N)ccc2F)C1]

A solution of tert-butyl 2-benzamido-7a-(5-bromo-2-fluoro-phenyl)-4,4a,5,7-tetrahydropyrrolo[3,4-d][1,3]thiazine-6-carboxylate (2.556 g, 4.8 mmol) and trans-N,N'-dimethyl-1,2-cyclohexanediamine (150 mg, 1.1 mmol) in ethanol (50 mL) is treated with sodium azide (933 mg, 14.3 mmol). An aqueous solution of L-ascorbic acid sodium salt (0.66 M, 3.2 mL, 2.1 mmol) and water (1 mL) are added and the top of the flask is purged with nitrogen. The mixture is treated with an aqueous solution of copper(II)sulfate pentahydrate (0.33 M, 3.2 mL, 1.1 mmol) and the mixture is immediately heated on a preheated hot plate at 80° C. for 1.5 hrs under nitrogen. A homogeneous mixture is obtained upon heating. The reaction is cooled, diluted with ice water, and the mixture is extracted with ethyl acetate (3×). The organic layers are combined and dried over sodium sulfate, filtered, and the solvent removed in vacuo to give the crude azide product. The crude azide product is combined with 10% palladium on carbon (1 g) in cold ethanol (150 mL) and the mixture is purged using vacuum/nitrogen and then vacuum/hydrogen. The mixture is stirred at room temperature under 30 psi of hydrogen for 5 hours. The reaction is vented, filtered through diatomaceous earth, and the filter cake rinsed with dichloromethane. Remove the solvent from the filtrate in vacuo and purify the crude product over silica gel with 50% ethyl acetate in dichloromethane to afford the titled compound (2.014 g, 89%). ES/MS (m/e): 471 (M+H).

Preparation 23 tert-Butyl (4aR,7aS)-2-benzamido-7a-[3-[(5-fluoro-pyridine-2-carbonyl)amino]phenyl]-4,4a,5,7-tetrahydropyrrolo[3,4-d][1,3]thiazine-6-carboxylate

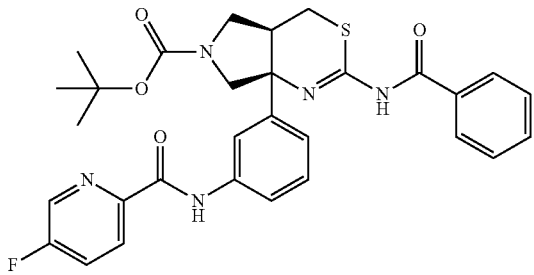 [SMILES: CC(C)(C)OC(=O)N1C[C@H]2CSC(NC(=O)c3ccccc3)=N[C@@]2(c2cccc(NC(=O)c3ccc(F)cn3)c2)C1]

A slurry of tert-butyl (4aR,7aS)-7a-(3-aminophenyl)-2-benzamido-4,4a,5,7-tetrahydropyrrolo[3,4-d][1,3]thiazine-6-carboxylate (93 mg, 0.21 mmol), 5-fluoropyridine-2-carboxylic acid (31.9 mg, 0.23 mmol), 1-hydroxybenzotriazole hydrate (56.7 mg, 0.41 mmol) and 1-(2-dimethylaminopropyl)-3-ethylcarbodiimide hydrochloride (40 mg, 0.21 mmol) in dichloromethane (4 mL) containing dimethylformamide (1 ml) is treated with diisopropylethylamine (179.2 μL, 1.03 mmol) and the resulting mixture is stirred at room temperature overnight. The reaction mixture is diluted with dichloromethane (5 mL) and saturated aqueous sodium bicarbonate (15 mL). The organic layer is separated and washed with saturated aqueous sodium chloride (10 mL), dried over sodium sulfate, filtered, and the solvent removed in vacuo to give the crude title compound (105 mg, 89%). ES/MS (m/e): 576 (M+H).

Preparation 24

N-[3-[(4aR,7aS)-2-Benzamido-4a,5,6,7-tetrahydro-4H-pyrrolo[3,4-d][1,3]thiazin-7a-yl]phenyl]-5-fluoro-pyridine-2-carboxamide; 2,2,2-trifluoroacetic acid

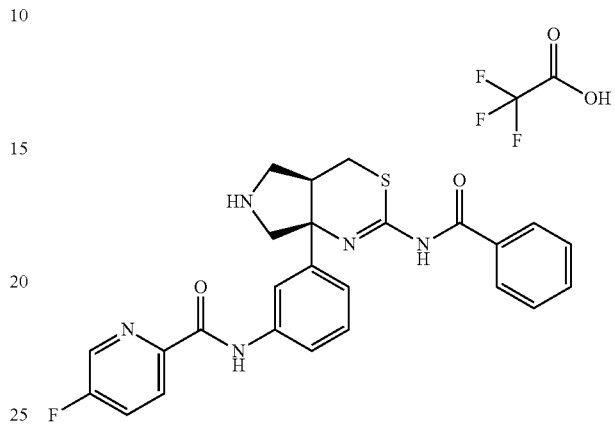

tert-Butyl (4aR,7aS)-2-benzamido-7a-[3-[(5-fluoropyridine-2-carbonyl)amino]phenyl]-4,4a,5,7-tetrahydropyrrolo[3,4-d][1,3]thiazine-6-carboxylate (105 mg, 0.18 mmol) is dissolved in dichloromethane (2 mL) and treated with trifluoroacetic acid (500 μL, 6.6 mmol). The resulting yellow solution is stirred for 4 hours at room temperature and the solvent removed in vacuo to give the crude title product (190 mg, 100%). ES/MS (m/e): 476 (M+H).

Preparation 25

N-[(4aR,7aS)-7a-(3-Aminophenyl)-4a,5,6,7-tetrahydro-4H-pyrrolo[3,4-d][1,3]thiazin-2-yl]benzamide

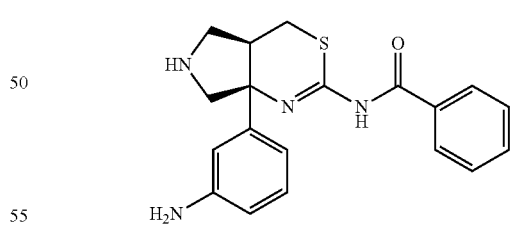

Trifluoroacetic acid (25 mL) is added to a solution of tert-butyl (4aR,7aS)-7a-(3-aminophenyl)-2-benzamido-4,4a,5,7-tetrahydropyrrolo[3,4-d][1,3]thiazine-6-carboxylate (4 g, 8.84 mmol) in dichloromethane (100 mL) and the mixture is stirred at room temperature under nitrogen for 4 hours. The solvent is removed in vacuo and the crude product is purified with an SCX column using 3:1 dichloromethane:methanol and then 2:1 dichloromethane:7 N ammonia in methanol to give the title compound (2.49 g, 80%). ES/MS (m/e): 353 (M+H).

Preparation 26

N-[7a-(5-Amino-2-fluoro-phenyl)-4a,5,6,7-tetrahydro-4H-pyrrolo[3,4-d][1,3]thiazin-2-yl]benzamide

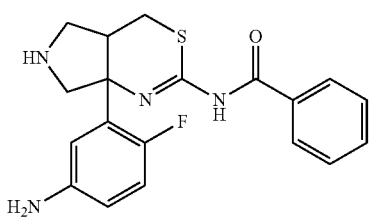 [SMILES: Nc1ccc(F)c(C23CNCC2CSC(NC(=O)c2ccccc2)=N3)c1]

Trifluoroacetic acid (10 mL) is added to a solution of tert-butyl 7a-(5-amino-2-fluoro-phenyl)-2-benzamido-4,4a,5,7-tetrahydropyrrolo[3,4-d][1,3]thiazine-6-carboxylate (2.013 g, 4.28 mmol) in dichloromethane (30 mL) and the mixture is stirred at room temperature under nitrogen for 4 hours. The solvent removed in vacuo and the crude product is purified with an SCX column using 3:1 dichloromethane: methanol and then 2:1 dichloromethane:7 N ammonia in methanol to give the title compound (1.555 g, 98%). ES/MS (m/e): 371 (M+H).

Preparation 27

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide

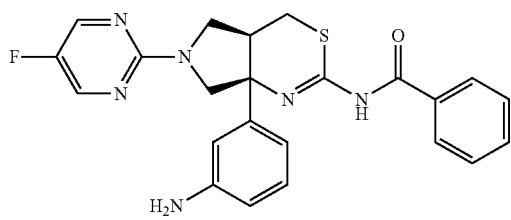

A solution of N-[(4aR,7aS)-7a-(3-aminophenyl)-4a,5,6,7-tetrahydro-4H-pyrrolo[3,4-d][1,3]thiazin-2-yl]benzamide (2.49 g, 7.06 mmol), 5-fluoro-2-chloropyrimidine (3.74 g, 28.26 mmol), and diisopropylethylamine (6.16 mL, 35.32 mmol) in 1,4-dioxane (60 mL) is heated to reflux for 4 hours under nitrogen. The reaction is cooled, diluted with water and extracted with ethyl acetate (3×). The combined organic extracts are dried over sodium sulfate, filtered and the solvent is removed in vacuo to give the crude product. The crude product is purified over silica gel with a 25 minute 5% to 100% ethyl acetate in hexanes gradient to give the title compound (2.51 g, 79%). ES/MS (m/e): 449 (M+H).

Preparation 28

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-5-fluoro-pyridine-2-carboxamide

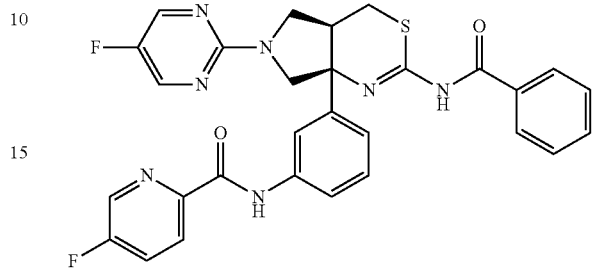

A solution of N-[3-[(4aR,7aS)-2-benzamido-4a,5,6,7-tetrahydro-4H-pyrrolo[3,4-d][1,3]thiazin-7a-yl]phenyl]-5-fluoro-pyridine-2-carboxamide; 2,2,2-trifluoroacetic acid (150 mg, 254 µmol), 5-fluoro-2-chloropyrimidine (68 mg, 51 µmol) and diisopropylethylamine (98 µL, 56 µmol) is heated in dimethyl sulfoxide (5 mL) overnight at 40° C. Additional 5-fluoro-2-chloropyrimidine (68 mg, 51 µmol) and diisopropylethylamine (98 µL, 56 µmol) is added and the mixture is heated overnight at 50° C. Additional 5-fluoro-2-chloropyrimidine (68 mg, 51 µmol) and diisopropylethylamine (98 µL, 56 µmol) is added and the mixture is heated overnight at 50° C. for a third night. The reaction is cooled, diluted with saturated aqueous sodium carbonate (50 mL) to give a slurry that is filtered and dried in a vacuum oven at 50° C. for 4 hours to give the title compound (60 mg, 41%). ES/MS (m/e): 449 (M+H).

Alternate Preparation 28

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide (282 mg, 628.73 µmol) and 5-fluoropyridine-2-carboxylic acid (106.46 mg, 754.47 µmol) are combined in dichloromethane (3 mL) and dimethylformamide (0.5 mL). 1-Hydroxybenzotriazole (112.70 mg, 817.35 µmol) and then 1-(3-dimethylaminopropyl)-3-ethylcarbodiimide hydrochloride (159.07 mg, 817.35 µmol) is added and the resulting mixture is stirred for 5 hours at room temperature under nitrogen. The reaction mixture is diluted with water and the pH is adjusted with 1 N NaOH to ~12. The mixture is extracted with ethyl acetate (3×). The organic extracts are combined, dried over sodium sulfate, filtered and the solvent removed in vacuo to give the crude product. The crude product is purified over silica gel with a 20 minute 5% to 100% ethyl acetate in hexanes gradient to give the title compound (327 mg, 91%). ES/MS (m/e): 571 (M+H).

Preparation 29

N-[7a-(5-Amino-2-fluoro-phenyl)-6-(5-fluoropyrimidin-2-yl)-4,4a,5,7-tetrahydropyrrolo[3,4-d][1,3]thiazin-2-yl]benzamide

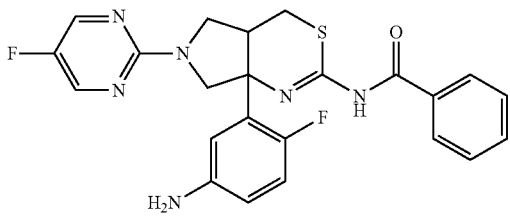 [SMILES: Nc1ccc(F)c(C23CN(c4ncc(F)cn4)CC2CSC(NC(=O)c2ccccc2)=N3)c1]

A solution of N-[7a-(5-amino-2-fluoro-phenyl)-4a,5,6,7-tetrahydro-4H-pyrrolo[3,4-d][1,3]thiazin-2-yl]benzamide (705 mg, 1.90 mmol), 5-fluoro-2-chloropyrimidine (1.01 g, 7.61 mmol), and diisopropylethylamine (1.66 mL, 9.52 mmol) are heated in 1,4-dioxane (20 mL) to reflux for 4 hours under nitrogen. The reaction is cooled, diluted with water, and extracted with ethyl acetate (3×). The organic layers are combined, dried over sodium sulfate, filtered and the solvent removed in vacuo to give crude product. The crude product is purified over silica gel with a 25 minute 5% to 100% ethyl acetate in hexanes gradient to give the title compound (590 mg, 66%). ES/MS (m/e): 467 (M+H).

Preparation 30

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-5-methoxy-pyrazine-2-carboxamide

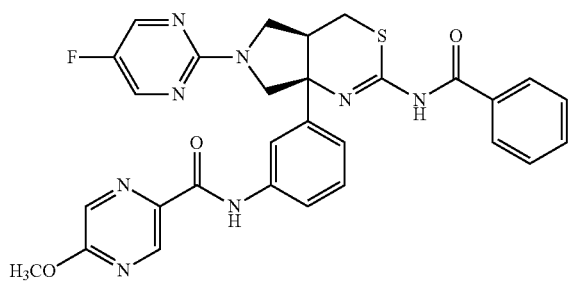 [SMILES: COc1cnc(C(=O)Nc2cccc([C@]34CN(c5ncc(F)cn5)C[C@H]3CSC(NC(=O)c3ccccc3)=N4)c2)cn1]

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide (400 mg, 891.81 µmole) and 5-methoxypyrazine-2-carboxylic acid (165 mg, 1.07 mmol) are combined in dichloromethane (4 mL) and dimethylformamide (0.5 mL). 1-Hydroxybenzotriazole (160 mg, 1.16 mmol) and then 1-(3-dimethylaminopropyl)-3-ethylcarbodiimide hydrochloride (226 mg, 1.16 mmol) are added and the resulting mixture is stirred for 5 hours at room temperature under nitrogen. The reaction mixture is diluted with water and the pH is adjusted to ~12 with 1 N NaOH. The mixture is extracted with ethyl acetate (3×). The combined organic extracts are dried over sodium sulfate, filtered and the solvent removed in vacuo. The crude product is purified over silica gel with a 20 minute 5% to 100% ethyl acetate in hexanes gradient to give the title compound (482 mg, 92%). ES/MS (m/e): 585 (M+H).

Preparation 31

N-[3-[2-Benzamido-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide

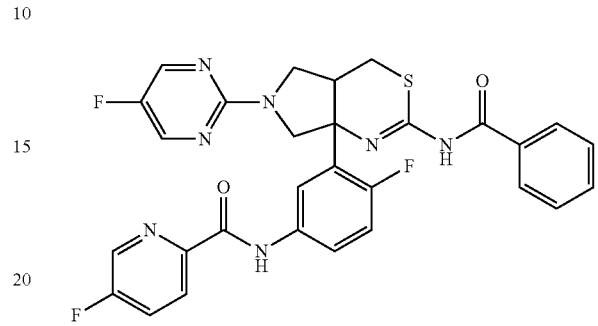

N-[7a-(5-Amino-2-fluoro-phenyl)-6-(5-fluoropyrimidin-2-yl)-4,4a,5,7-tetrahydropyrrolo[3,4-d][1,3]thiazin-2-yl]benzamide (302 mg, 647 µmol) and 5-fluoropyridine-2-carboxylic acid (110 mg, 777 µmol) are combined in dichloromethane (3 mL) and dimethylformamide (0.5 mL). 1-Hydroxybenzotriazole (116 mg, 842 µmol) and then 1-(3-dimethylaminopropyl)-3-ethylcarbodiimide hydrochloride (164 mg, 842 µmol) are added and the mixture is stirred overnight at room temperature under nitrogen. The reaction mixture is diluted with water and the pH adjusted with 1 N NaOH to ~12 and then extracted with ethyl acetate (3×). The organic layers are combined and filtered to collect the insoluble material. The solids are washed with water and ethyl acetate and dried under vacuum to give the title compound. The organic layer from the filtrate is dried over sodium sulfate, filtered and the solvent removed in vacuo. The residue is purified over silica gel with a 20 minute 5% to 100% ethyl acetate in hexanes gradient to give additional title compound with a combined yield (275 mg, 72%). ES/MS (m/e): 590 (M+H).

Preparation 32

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide, (isomer 1)

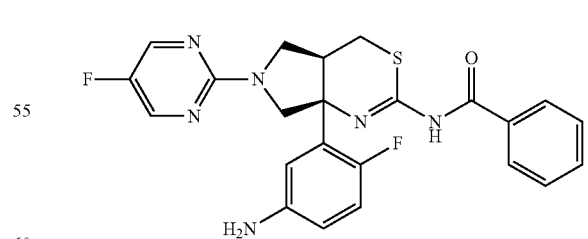

Racemic N-[7a-(5-amino-2-fluoro-phenyl)-6-(5-fluoropyrimidin-2-yl)-4,4a,5,7-tetrahydropyrrolo[3,4-d][1,3]thiazin-2-yl]benzamide (1.694 g, 3.63 mmol) is chirally purified by HPLC (Column: Chiralcel OJ, 8×35 cm; eluent: 90% methanol (0.2% dimethylethylamine) and 10% acetonitrile; flow 400 mL/min at UV 280 nm). Analysis of the first eluting isomer (Column: Chiralcel OJ-H 0.46×15 cm; eluent: 10:90 acetonitrile:methanol (with 0.2% dimethylethylamine); flow: 0.6 mL/min at UV 280 nm) confirms the enantiomerically enriched (99% ee) enantiomer with R$_t$=6.70 minutes, (723 mg, 43%). ES/MS (m/e): 467 (M+H).

Preparation 33

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide, (isomer 1)

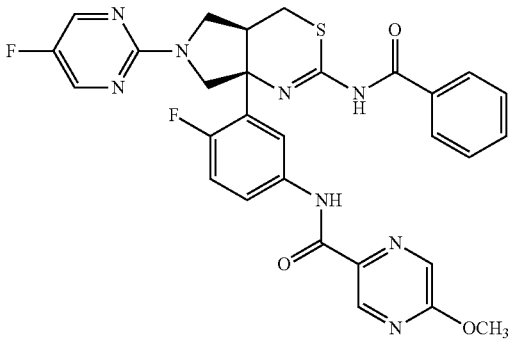 [SMILES: COc1cnc(C(=O)Nc2ccc(F)c([C@]34CN(c5ncc(F)cn5)C[C@H]3CSC(NC(=O)c3ccccc3)=N4)c2)cn1]

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide (0.361 g, 0.77 mmol, isomer 1) is dissolved in a mixture of dichloromethane (4 mL) and DMF (0.5 mL). 5-Methoxypyrazine-2-carboxylic acid (240 mg, 1.55 mmol), 1-hydroxybenzotriazole (210 mg, 1.55 mmol) and 1-(3-dimethylaminopropyl)-3-ethylcarbodiimide hydrochloride (300 mg, 1.55 mmol) are added to the mixture and the mixture is stirred overnight at room temperature. The reaction solution is added directly onto a 12 g silica gel loading column and purified using a 40 g silica gel column and eluting with a 0-100% ethyl acetate/hexanes gradient. The product is dissolved in ethyl acetate (200 mL), washed with 1 N NaOH (2×50 mL), and with brine (1×50 mL). The silica gel purification is repeated as described above to give the title compound (350 mg, 74%). ES/MS (m/e): 603 (M+H).

Preparation 34

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-5-cyano-pyridine-2-carboxamide

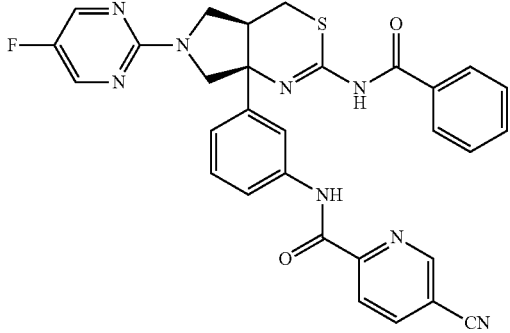 [SMILES: N#Cc1ccc(C(=O)Nc2cccc([C@]34CN(c5ncc(F)cn5)C[C@H]3CSC(NC(=O)c3ccccc3)=N4)c2)nc1]

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide (0.30 g, 0.67 mmol) is dissolved in dichloromethane (10 mL) and 5-cyanopyridine-2-carboxylic acid (129 mg, 0.87 mmol), 1-hydroxybenzotriazole (185 mg, 1.34 mmol) and 1-(3-dimethylaminopropyl)-3-ethylcarbodiimide hydrochloride (169 mg, 0.87 mmol) are added. Diisopropylethyamine (0.35 mL, 2 mmol) is added and the reaction is stirred at room temperature overnight. The material is purified directly with silica gel chromatography eluting with a 0-100% ethyl acetate/hexanes gradient to give the title compound (360 mg, 88%). ES/MS (m/e): 579 (M+H).

Preparation 35

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-3,5-difluoro-pyridine-2-carboxamide

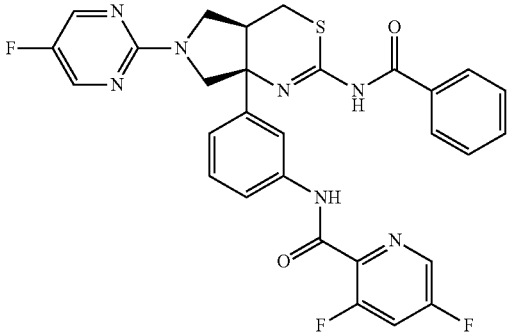 [SMILES: O=C(NC1=N[C@@]2(c3cccc(NC(=O)c4ncc(F)cc4F)c3)CN(c3ncc(F)cn3)C[C@H]2CS1)c1ccccc1]

N-[(4aR,7aS)-7a-(3-Aminophenyl)-6-(5-fluoropyrimidin-2-yl)-4,4a,5,7-tetrahydropyrrolo[3,4-d][1,3]thiazin-2-yl]benzamide (0.30 g, 0.67 mmol) is dissolved in dichloromethane (10 mL) and 3,5-difluoropyridine-2-carboxylic acid (138 mg, 0.87 mmol), 1-hydroxybenzotriazole (185 mg, 1.34 mmol) and 1-(3-dimethylaminopropyl)-3-ethylcarbodiimide hydrochloride (169 mg, 0.87 mmol) are added. Diisopropylethylamine (0.35 mL, 2 mmol) is added and the reaction is stirred at room temperature overnight. The reaction is purified directly with silica gel chromatography eluting with a 0-100% ethyl acetate/hexanes gradient to give the title compound (330 mg, 84%). ES/MS (m/e): 590 (M+H).

Preparation 36

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-cyano-pyridine-2-carboxamide, (isomer 1)

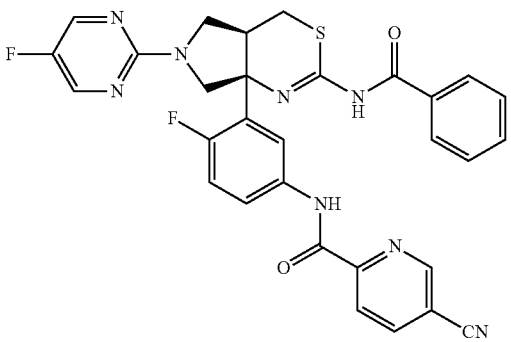 [SMILES: N#Cc1ccc(C(=O)Nc2ccc(F)c([C@]34CN(c5ncc(F)cn5)C[C@H]3CSC(NC(=O)c3ccccc3)=N4)c2)nc1]

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide (0.180 g, 0.39 mmol, isomer 1) is dissolved in a mixture of dichloromethane (2 mL) and DMF (0.25 mL). 5-Cyanopyridine-2-carboxylic acid (114 mg, 0.77 mmol), 1-hydroxybenzotriazole (106 mg, 0.77 mmol) and 1-(3-dimethylaminopropyl)-3-ethylcarbodiimide hydrochloride (150 mg, 0.77 mmol) are added and the reaction is stirred at room temperature overnight. The mixture is diluted with water (10 mL), ethyl acetate (10 mL) and added to a solution of 1 N NaOH (100 mL). The mixture is extracted with EtOAc (2×100 mL) and the organic layers are combined and washed with brine. The organic layer is dried over $MgSO_4$, filtered and concentrated. The residue is purified over silica gel chromatography using a 0-100% ethyl acetate/hexanes gradient to give the title compound (133 mg, 57%). ES/MS (m/e): 597 (M+H).

Preparation 37

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-3,5-difluoro-pyridine-2-carboxamide, (isomer 1)

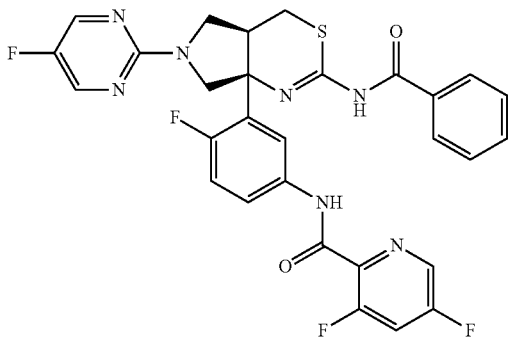 [SMILES: O=C(NC1=N[C@@]2(c3cc(NC(=O)c4ncc(F)cc4F)ccc3F)CN(c3ncc(F)cn3)C[C@H]2CS1)c1ccccc1]

N-[(4aR,7aS)-7a-(5-Amino-2-fluoro-phenyl)-6-(5-fluoropyrimidin-2-yl)-4,4a,5,7-tetrahydropyrrolo[3,4-d][1,3]thiazin-2-yl]benzamide (0.180 g, 0.39 mmol, isomer 1) is dissolved in a mixture of dichloromethane (2 mL) and DMF (0.25 mL). 5-Cyanopyridine-2-carboxylic acid (114 mg, 0.77 mmol), 1-hydroxybenzotriazole (106 mg, 0.77 mmol) and 1-(3-dimethylaminopropyl)-3-ethylcarbodiimide hydrochloride (150 mg, 0.77 mmol) are added and the reaction is stirred at room temperature overnight. The mixture is diluted with water (10 mL) and ethyl acetate (10 mL) and then poured into a solution of 1 N NaOH (100 mL). The mixture is extracted with EtOAc (2×100 mL) the organic extracts are combined and washed with brine. The organic layers are dried over $MgSO_4$, filtered and concentrated. The residue is purified via silica gel chromatography using a 0-100% ethyl acetate/hexanes gradient to give the title compound (190 mg, 80%). ES/MS (m/e): 608 (M+H).

Example A

N-[3-[2-Amino-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide

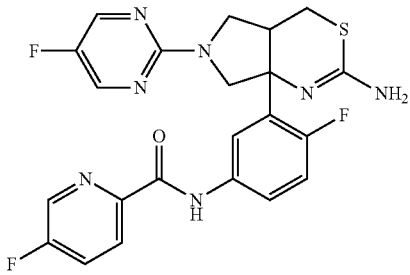 [SMILES: NC1=NC2(c3cc(NC(=O)c4ccc(F)cn4)ccc3F)CN(c3ncc(F)cn3)CC2CS1]

A mixture of N-[3-[2-benzamido-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide (293 mg, 497 µmol), O-methylhydroxylamine hydrochloride (430 mg, 4.97 mmol) and pyridine (402 µL, 4.97 mmol) is heated in ethanol (13 mL) to 70° C. in a capped flask for 2.5 hours. Dimethyl sulfoxide (3 mL) is added and the mixture is heated at 70° C. overnight. Additional dimethyl sulfoxide (10 mL) is added and heating continued at 70° C. for 4 hours. Additional O-methylhydroxylamine hydrochloride (208 mg, 2.48 mmol) and pyridine (201 µL, 2.48 mmol) is added and the mixture is heated to 60° C. for 3 hours and the mixture is stirred for 3 days at room temperature. In a separate flask, a mixture of N-[3-[2-benzamido-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide (276 mg, 468 µmol), O-methylhydroxylamine hydrochloride (405 mg, 4.68 mmol) and pyridine (478 µL, 4.68 mmol) is heated in ethanol (15 mL) and dimethyl sulfoxide (4 mL) at 70° C. in a capped flask overnight. Additional dimethyl sulfoxide (10 mL) is added and heating is continued at 70° C. for 4 hours. Additional O-methylhydroxylamine hydrochloride (195 mg, 2.34 mmol) and pyridine (189 µL, 2.34 mmol) is added and heating continued at 70° C. for 3 hours followed by stirring the mixture for 3 days at room temperature. The two reaction mixtures are combined and most of the solvent removed in vacuo. The crude product is purified on a SCX column using 3:1 dichloromethane:methanol and then 2:1 dichloromethane:7 N ammonia in methanol. The crude product is further purified over silica gel with a 20 minute 0.5% to 10% gradient of 7 N ammonia methanol in dichloromethane gradient to give the title compound (451 mg, 96%). ES/MS (m/e): 486 (M+H).

Example 1

N-{3-[(4aR,7aS)-2-Amino-6-(5-fluoropyrimidin-2-yl)-4a,5,6,7-tetrahydropyrrolo[3,4-d][1,3]thiazin-7a(4H)-yl]phenyl}-5-fluoropyridine-2-carboxamide hydrochloride

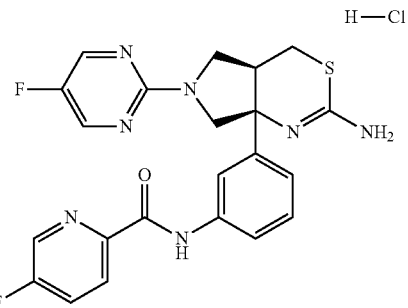

A mixture of N-[3-[(4aR,7aS)-2-benzamido-6-(5-fluoropyrimidin-2-yl)-4,4a,5,7-tetrahydropyrrolo[3,4-d][1,3]thiazin-7a-yl]phenyl]-5-fluoro-pyridine-2-carboxamide (320 mg, 560 µmol), O-methylhydroxylamine hydrochloride (485 mg, 5.60 mmol) and pyridine (453 µL, 5.60 mmol) in ethanol (15 mL) is heated at 65° C. in a capped vial for five hours. The reaction is cooled and the solvent removed in vacuo. The crude product is purified over silica gel with a 30 minute 0.5% to 10% gradient of 7 N ammonia in methanol dichloromethane gradient to give N-[3-[(4aR,7aS)-2-amino-6-(5- fluoropyrimidin-2-yl)-4,4a,5,7-tetrahydropyrrolo[3,4-d][1,3]thiazin-7a-yl]phenyl]-5-fluoro-pyridine-2-carboxamide (219 mg, 84%). This material is dissolved in dichloromethane (1 mL) and methanol (0.5 mL) and 1 M hydrogen chloride in diethyl ether (0.47 mL, 470 µmol) is added. The solvent is removed in vacuo to give the title compound (228 mg, 81%). ES/MS (m/e): 468 (M+H).

Example 2

N-{3-[(4aR,7aS)-2-Amino-6-(5-fluoropyrimidin-2-yl)-4a,5,6,7-tetrahydropyrrolo[3,4-d][1,3]thiazin-7a(4H)-yl]phenyl}-5-methoxypyrazine-2-carboxamide hydrochloride

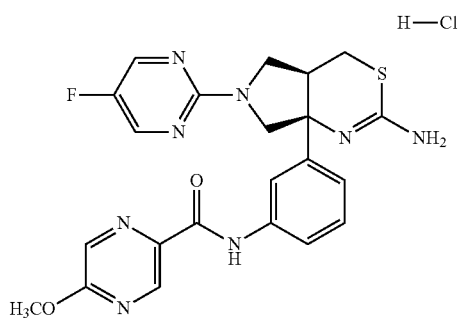

A mixture of N-[3-[(4aR,7aS)-2-benzamido-6-(5-fluoropyrimidin-2-yl)-4,4a,5,7-tetrahydropyrrolo[3,4-d][1,3]thiazin-7a-yl]phenyl]-5-methoxy-pyrazine-2-carboxamide (479 mg, 819 µmol), O-methylhydroxylamine hydrochloride (709 mg, 8.19 mmol) and pyridine (663 µL, 8.19 mmol) in ethanol (20 mL) is heated at 50° C. in a capped flask overnight. Dimethyl sulfoxide (4 mL) is added and the mixture is heated to 70° C. for 4 hours to obtain a solution. The reaction is cooled and most of the solvent is removed in vacuo. Water is added and the pH is adjusted to ~12 with 1 N sodium hydroxide. The mixture is extracted with ethyl acetate (5×). The combined organic extracts are dried over sodium sulfate, filtered and the solvent removed in vacuo. The crude product is purified over silica gel with a 30 minute 0.5% to 10% gradient of 7 N ammonia methanol in dichloromethane gradient. The mixture is purified again on a SCX column using 3:1 dichloromethane:methanol and then 2:1 dichloromethane:7 N ammonia in methanol to remove residual dimethyl sulfoxide. The mixture is purified a final time over silica gel with a 20 minute 0.5% to 10% gradient of 7 N ammonia methanol in dichloromethane to give N-[3-[(4aR,7aS)-2-amino-6-(5-fluoropyrimidin-2-yl)-4,4a,5,7-tetrahydropyrrolo[3,4-d][1,3]thiazin-7a-yl]phenyl]-5-methoxy-pyrazine-2-carboxamide. This material is dissolved in dichloromethane (1 mL) and methanol (0.5 mL) and 1 M hydrogen chloride in diethyl ether (0.66 mL, 660 µmol) is added. The solvent is removed in vacuo to give the title compound (329 mg, 78%). ES/MS (m/e): 481 (M+H).

Example 3

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide hydrochloride

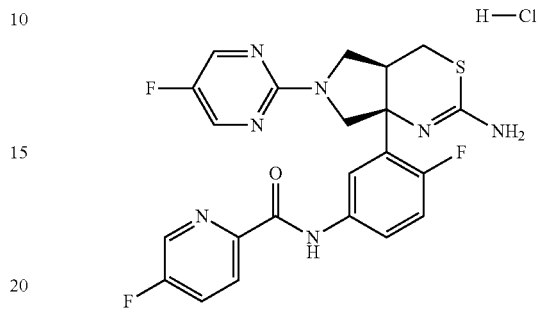

Racemic N-[3-[2-amino-6-(5-fluoropyrimidin-2-yl)-4,4a,5,7-tetrahydropyrrolo[3,4-d][1,3]thiazin-7a-yl]-4-fluoro-phenyl]-5-fluoro-pyridine-2-carboxamide (451 mg, 929 µmol) is chirally purified by SFC (Column: Chiralcel OD-H (5 um), 2.1×25 cm; eluent: 40% methanol (0.2% isopropylamine) in CO$_2$; flow 70 mL/min at UV 225 nm). Chiral analysis of the first eluting isomer: Column: Chiralcel OD-H (5 µm), 4.6×150 mm; eluent: 40% methanol (0.2% isopropylamine) in CO$_2$; flow 5 mL/min at UV 225 nm confirms the enantiomerically enriched (>99% ee) enantiomer with $R_t$=1.01 minutes (175 mg, 360 µmoles). This material (free base, isomer 1) is dissolved in dichloromethane (1 mL) and methanol (0.5 mL) and 1 M hydrogen chloride in diethyl ether (0.36 mL, 360 µmoles) is added. The solvent is removed in vacuo to give the title compound (183 mg, 38%). ES/MS (m/e): 486 (M+H).

Example 4

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide hydrochloride

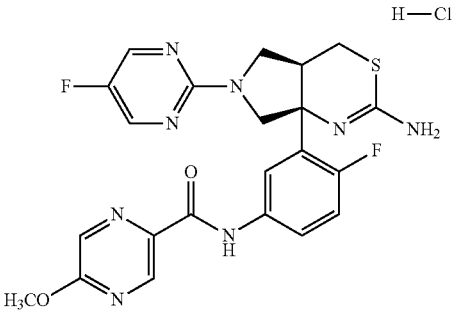

N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-methoxy-pyrazine-2-carboxamide (0.350 g, 0.58 mmol, isomer 1) is dissolved in THF (2 mL) and then methanol (4 mL) and ethanol (4 mL) are added. O-Methylhydroxylamine hydrochloride (495 mg, 5.81 mmol) and pyridine (470 µL, 5.81 mmol) are added to the mixture and the reaction is warmed to 50° C. and stirred overnight. Silica gel (~10 g) is added to the reaction and the mixture is concentrated. The sample, dried onto silica gel, is loaded onto an empty cartridge and purified eluting with a 0-10% gradient of 7 N ammonia methanol in dichloromethane. The product is purified a second time on a SCX column using 3:1 dichloromethane:methanol and then 2:1 dichloromethane:7 N ammonia in methanol. The product is purified a final time over silica gel with a 0% to 10% gradient of 7 N ammonia methanol in dichloromethane to give the free base of the title compound. This material is dissolved in dichloromethane (5 mL) and 1 M hydrogen chloride in diethyl ether (0.20 mL, 660 µmol) is added. The solvent is removed in vacuo to give the title compound (71 mg, 23%). ES/MS (m/e): 498 (M+H).

Example 5

N-[3-[(4aR,7aS)-2-Amino-6-(5-fluoropyrimidin-2-yl)-4,4a,5,7-tetrahydropyrrolo[3,4-d][1,3]thiazin-7a-yl]phenyl]-5-cyano-pyridine-2-carboxamide hydrochloride

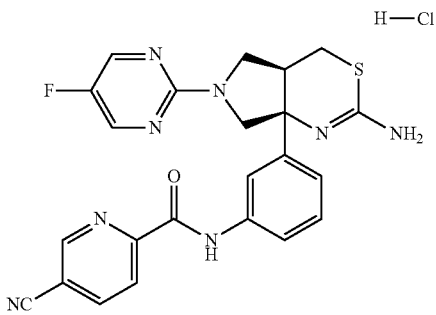

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-5-cyano-pyridine-2-carboxamide (360 mg, 0.59 mmol) is dissolved in ethanol (10 mL) and dichloromethane (2 mL). 0-Methylhydroxylamine hydrochloride (504 mg, 5.91 mmol) and pyridine (478 µL, 5.91 mmol) are added and the reaction is stirred at room temperature over the weekend (70 hrs). The reaction is warmed to 60° C. and stirred for 24 hrs. The reaction is concentrated to give the crude product and purified via silica gel chromatography using a 0-10% gradient of 7 N ammonia methanol in dichloromethane to give the free base of the title compound. This material is dissolved in dichloromethane (5 mL) and 1 M hydrogen chloride in diethyl ether (0.54 mL, 540 µmol) is added. The solvent is removed in vacuo to give the title compound (240 mg, 75%). ES/MS (m/e): 475 (M+H).

Example 6

N-[3-[(4aR,7aS)-2-Amino-6-(5-fluoropyrimidin-2-yl)-4,4a,5,7-tetrahydropyrrolo[3,4-d][1,3]thiazin-7a-yl]phenyl]-3,5-difluoro-pyridine-2-carboxamide hydrochloride

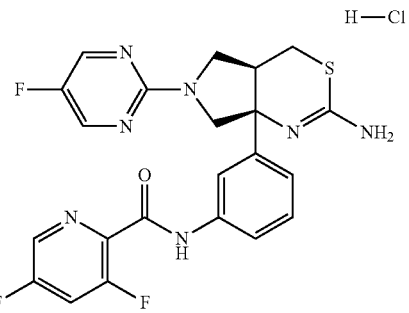

N-[3-[(4aR,7aS)-2-Benzamido-6-(5-fluoropyrimidin-2-yl)-4,4a,5,7-tetrahydropyrrolo[3,4-d][1,3]thiazin-7a-yl]phenyl]-3,5-difluoro-pyridine-2-carboxamide (330 mg, 0.53 mmol) is dissolved in THF (10 mL) and diluted with ethanol (10 mL). O-Methylhydroxylamine hydrochloride (453 mg, 5.32 mmol) and pyridine (430 µL, 5.91 mmol) are added and the reaction is stirred at room temperature over the weekend (70 hrs). The reaction is warmed to 60° C. and stirred for 24 hrs. The mixture is concentrated onto silica gel (~10 g) and purified via silica gel chromatography using a 0-10% gradient of 7 N ammonia methanol in dichloromethane to give the free base of the title compound. This material is dissolved in dichloromethane (5 mL) and 1 M hydrogen chloride in diethyl ether (0.49 mL, 490 µmol) is added. The solvent is removed in vacuo to give the title compound (159 mg, 54%). ES/MS (m/e): 486 (M+H).

Example 7

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-5-cyano-pyridine-2-carboxamide hydrochloride N-[3-[(4aR,7aS)-2-Benzamido-6-(5-fluoropyrimidin-2-yl)-4,4a,5,7-tetrahydropyrrolo[3,4-d][1,3]thiazin-7a-yl]-4-fluoro-phenyl]-5-cyano-pyridine-2-carboxamide (133 mg, 0.22 mmol, isomer 1) is dissolved in THF (1 mL) and diluted with methanol (3 mL) and ethanol (3 mL). O-Methylhydroxylamine hydrochloride (190 mg, 2.2 mmol) and pyridine (180 µL, 2.2 mmol) are added. The reaction is warmed to 50° C. and stirred overnight. The mixture is concentrated onto silica gel (~10 g) and purified via silica gel chromatography eluting with a 0-10% gradient of 7 N ammonia methanol in dichloromethane. The material is purified a second time on a SCX column using 3:1 dichloromethane:methanol and then 2:1 dichloromethane:7 N ammonia in methanol. The mixture is purified a final time over silica gel with a 0% to 10% gradient of 7 N ammonia methanol in dichloromethane to give the free base of the title compound. This material is dissolved in dichloromethane (5 mL) and 1 M hydrogen chloride in diethyl ether (0.27 mL, 270 µmol) is added. The solvent is removed in vacuo to give the title compound (114 mg, 97%). ES/MS (m/e): 493 (M+H).

Example 8

N-[3-[(4aR,7aS)-2-Amino-6-(5-fluoropyrimidin-2-yl)-4,4a,5,7-tetrahydropyrrolo[3,4-d][1,3]thiazin-7a-yl]-4-fluoro-phenyl]-3,5-difluoro-pyridine-2-carboxamide hydrochloride

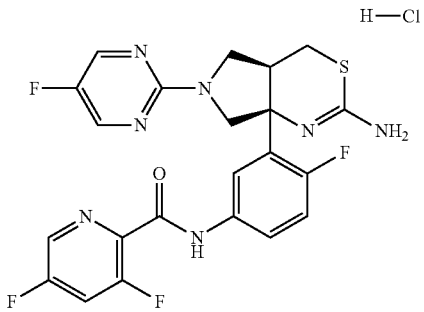

N-[3-[(4aR,7aS)-2-benzamido-6-(5-fluoropyrimidin-2-yl)-4,4a,5,7-tetrahydropyrrolo[3,4-d][1,3]thiazin-7a-yl]-4-fluoro-phenyl]-3,5-difluoro-pyridine-2-carboxamide (190 mg, 0.31 mmol, isomer 1) is dissolved in THF (1 mL) and diluted with methanol (3 mL) and ethanol (3 mL). O-Methylhydroxylamine hydrochloride (267 mg, 3.1 mmol) and pyridine (253 µL, 3.1 mmol) are added and the reaction is warmed to 50° C. and stirred overnight. The reaction is purified on an SCX column using 3:1 dichloromethane:methanol and then 2:1 dichloromethane:7 N ammonia in methanol. The material is purified a final time over silica gel with a 0% to 10% gradient of 7 N ammonia methanol in dichloromethane to give the free base of the title compound. This material is dissolved in dichloromethane (5 mL) and 1 M hydrogen chloride in diethyl ether (0.20 mL, 200 µmol) is added. The solvent is removed in vacuo to give the title compound (101 mg, 60%). ES/MS (m/e): 504 (M+H).

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 mM to 0.05 nM in a 96-well round-bottom plate before conducting the in vitro enzymatic and whole cell assays.

In Vitro Protease Inhibition Assays:

Expression of Human BACE1

Human BACE1 (accession number: AF190725) is cloned from total brain cDNA by RT-PCR. The nucleotide sequences corresponding to amino acid sequences #1 to 460 are inserted into the cDNA encoding human $IgG_1$ (Fc) polypeptide (Vassar et al. 1999). This fusion protein of BACE1(1-460) and human Fc, named huBACE1:Fc, is constructed into the pJB02 vector. Human BACE1(1-460):Fc (huBACE1:Fc) is transiently expressed in HEK293 cells. 250 µg cDNA of each construct is mixed with Fugene 6 and added to 1 liter HEK293 cells. Four days after the transfection, conditioned media are harvested for purification.

Purification of huBACE1:Fc huBACE1:Fc is purified by Protein A chromatography. The enzyme is stored at −80° C. in small aliquots.

BACE1 FRET Assay

Serial dilutions of test compounds are prepared as described above. Compounds are further diluted 20× in $KH_2PO_4$ buffer. Ten µL of each dilution is added to each well on row A to H of a corresponding low protein binding black plate containing the reaction mixture (25 µL of 50 mM $KH_2PO_4$, pH 4.6, 1 mM TRITON® X-100, 1 mg/mL Bovine Serum Albumin, and 15 µM of FRET substrate) (See Yang, et. al., *J. Neurochemistry*, 91(6) 1249-59 (2004)). The content is mixed well on a plate shaker for 10 minutes. Fifteen µL of two hundred pM human BACE1(1-460):Fc (See Vasser, et al., *Science*, 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $EC_{50}$ and $IC_{50}$ values. (See Sinha, et al., *Nature*, 402, 537-540 (2000)).

The following exemplified compounds were tested essentially as described above and exhibited the following activity for BACE1:

TABLE 1

| Example # | BACE1 $IC_{50}$ (nM) |
| --- | --- |
| 1 | 0.610 (±0.0948, n = 8/9) |
| 2 | 0.482 (±0.0580, n = 6/7) |
| 3 | 0.554 (±0.0674, n = 3) |
| 4 | 0.569 (±0.0796, n = 2) |
| 5 | 0.450 (±0.0911, n = 4) |
| 6 | 0.739 (±0.181, n = 7) |
| 7 | 0.358 (n = 1/3) |
| 8 | 0.730 (±0.0951, n = 3) |

Mean ± SEM;
SEM = standard error of the mean

These data demonstrate that the compounds of Table 1 potently inhibit purified recombinant BACE1 enzyme activity in vitro.

Whole Cell Assays for Measuring the Inhibition of Beta-Secretase Activity

HEK293Swe Whole Cell Assay

The routine whole cell assay for the measurement of inhibition of beta-secretase activity utilizes the human embryonic kidney cell line HEK293p (ATCC Accession No. CRL-1573) stably expressing a human APP751 cDNA containing the naturally occurring double mutation Lys651Met652 to Asn651Leu652, commonly called the Swedish mutation (noted HEK293Swe) and shown to overproduce Abeta (Citron, et al., *Nature*, 360, 672-674 (1992)). In vitro Abeta reduction assays have been described in the literature (See Dovey, et al., *Journal of Neurochemistry*, 76, 173-181 (2001); Seubert, et al., *Nature*, 361, 260 (1993); and Johnson-Wood, et al., *Proc. Natl. Acad. Sci. USA*, 94, 1550-1555 (1997)).

Cells (HEK293Swe at $3.5 \times 10^4$ cells/well, containing 200 μL culture media, DMEM containing 10% FBS) are incubated at 37° C. for 4 to 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The following exemplified compounds were tested essentially as described above and exhibited the following activity for Abeta lowering effect:

TABLE 2

| Example | HEK 293 Swe A-beta (1-40) ELISA $IC_{50}$ (nM) | HEK 293 Swe A-beta (1-42) ELISA $IC_{50}$ (nM) |
|---|---|---|
| 1 | 0.619 | 0.437 |
| 2 | 0.324 | 0.289 |
| 3 | 1.26 | 0.299 |
| 5 | 0.0887 | 0.0785 |
| 6 | 0.220 | 0.211 |

Mean ± SEM;
SEM = standard error of the mean

These data demonstrate that the compounds of Table 2 potently inhibit native Abeta production in whole cells.

PDAPP Primary Neuronal Assay

A confirmatory whole cell assay is also run in primary neuronal cultures generated from PDAPP transgenic embryonic mice. Primary cortical neurons are prepared from Embryonic Day 16 PDAPP embryos and cultured in 96 well plates ($15 \times 10^4$ cells/well in DMEM/F12 (1:1) plus 10% FBS). After 2 days in vitro, culture media is replaced with serum free DMEM/F12 (1:1) containing B27 supplement and 2 μM (final) of Ara-C (Sigma, C1768). At day 5 in vitro, neurons are incubated at 37° C. for 24 h in the presence/absence of inhibitors (diluted in DMSO) at the desired concentration. At the end of the incubation, conditioned media are analyzed for evidence of beta-secretase activity, for example, by analysis of Abeta peptides. Total Abeta peptides (Abeta 1-x) are measured by a sandwich ELISA, using monoclonal 266 as a capture antibody and biotinylated 3D6 as reporting antibody. Alternatively, Abeta 1-40 and Abeta 1-42 peptides are measured by a sandwich ELISA, using monoclonal 2G3 as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody. The concentration of Abeta released in the conditioned media following the compound treatment corresponds to the activity of BACE1 under such conditions. The 10-point inhibition curve is plotted and fitted with the four-parameter logistic equation to obtain the $EC_{50}$ and $IC_{50}$ values for the Abeta-lowering effect. The following exemplified compounds were tested essentially as described above and exhibited the following activity for Abeta lowering effect:

TABLE 3

| Example | PDAPP Neuron A-beta (1-40) ELISA $IC_{50}$ (nM) | PDAPP Neuron A-beta (1-42) ELISA $IC_{50}$ (nM) |
|---|---|---|
| 1 | 0.487 (±0.0946, n = 2) | 0.591 (±0.268, n = 2) |
| 2 | 0.244 (n = 1/2) | 1.22 (±0.967, n = 2) |
| 3 | 0.309 (±0.0478, n = 2) | 0.184 (±0.0234, n = 2) |
| 4 | 0.134 | 0.131 |
| 5 | 0.132 (±0.0717, n = 2) | 0.0813 |
| 6 | 0.279 (±0.0607, n = 2) | 0.308 (±0.115, n = 2) |
| 7 | 0.0873 | 0.0649 |
| 8 | 0.285 | 0.29 |

Mean ± SEM;
SEM = standard error of the mean

These data demonstrate that the compounds of Table 3 potently inhibit Abeta production in whole cells In Vivo Inhibition of Beta-Secretase Several animal models, including mouse, guinea pig, dog, and monkey, may be used to screen for inhibition of beta-secretase activity in vivo following compound treatment Animals used in this invention can be wild type, transgenic, or gene knockout animals. For example, the PDAPP mouse model, prepared as described in Games et al., Nature 373, 523-527 (1995), and other non-transgenic or gene knockout animals are useful to analyze in vivo inhibition of Abeta and sAPPbeta production in the presence of inhibitory compounds. Generally, 2 to 12 month old PDAPP mice, gene knockout mice or non-transgenic animals are administered compound formulated in vehicles, such as corn oil, cyclodextran, phosphate buffers, PHARMASOLVE®, or other suitable vehicles. One to twenty-four hours following the administration of compound, animals are sacrificed, and brains as well as cerebrospinal fluid and plasma are removed for analysis of Abetas, C99, and sAPP fragments. (See May, et al., *Journal of Neuroscience*, 31, 16507-16516 (2011)).

For standard in vivo pharmacology studies, animals are dosed with various concentrations of compound and compared to a vehicle-treated control group dosed at the same time. For some time course studies, brain tissue, plasma, or cerebrospinal fluid is obtained from selected animals, beginning at time 0 to establish a baseline. Compound or appropriate vehicle is administered to other groups and sacrificed at various times after dosing. Brain tissue, plasma, or cerebrospinal fluid is obtained from selected animals and analyzed for the presence of APP cleavage products, including Abeta peptides, sAPPbeta, and other APP fragments, for example, by specific sandwich ELISA assays. At the end of the test period, animals are sacrificed and brain tissues, plasma, or cerebrospinal fluid are analyzed for the presence of Abeta peptides, C99, and sAPPbeta, as appropriate. Brain tissues of APP transgenic animals may also be analyzed for the amount of beta-amyloid plaques following compound treatment. "Abeta 1-x peptide" as used herein refers to the sum of Abeta species that begin with residue 1 and ending with a C-terminus greater than residue 28. This detects the majority of Abeta species and is often called "total Abeta".

Animals (PDAPP or other APP transgenic or non-transgenic mice) administered an inhibitory compound may demonstrate the reduction of Abeta or sAPPbeta in brain tissues, plasma or cerebrospinal fluids and decrease of beta amyloid plaques in brain tissue, as compared with vehicle-treated controls or time zero controls. For example, 3 hours after administration of 1, 3, or 10 mg/kg oral dose of the compound of Example 1 to young female PDAPP mice, Abeta 1-x peptide levels are reduced approximately 34%, 48%, and 53% in brain hippocampus, and approximately 43%, 59% and 66% in brain cortex, respectively, compared to vehicle-treated mice.

For example, 3 hours after administration of 1 or 3 mg/kg oral dose of the compound of Example 3, Abeta 1-x peptide levels are reduced approximately 38% and 50% in brain hippocampus, and approximately 34% and 53% in brain cortex, respectively compared to vehicle-treated mice.

Given the activity of Examples 1 and 3 against BACE enzyme in vitro, these Abeta lowering effects are consistent with BACE inhibition in vivo, and further demonstrate CNS penetration of Examples 1 and 3

These studies show that compounds of the present invention inhibit BACE and are, therefore, useful in reducing Abeta levels.

We claim:

1. A compound of the formula:

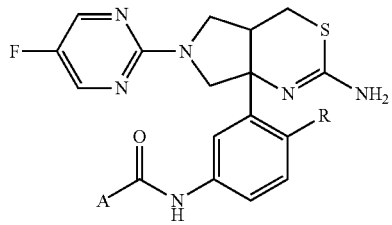

wherein R is H or F; and
A is:

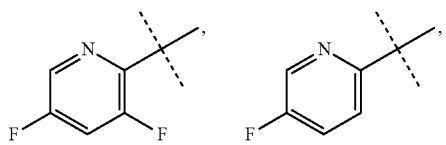

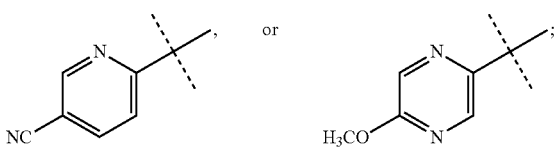

or a pharmaceutically acceptable salt thereof.

2. The compound or salt according to claim 1 which is:

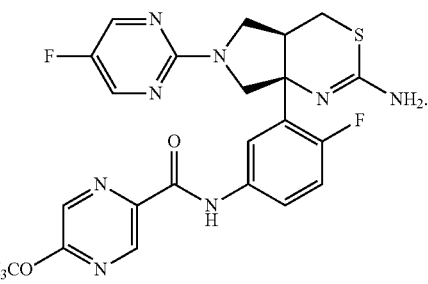

3. The compound according to claim 2 which is:

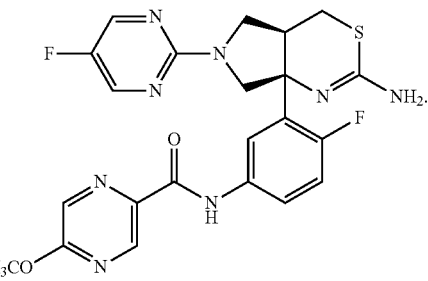

4. A method of treating Alzheimer's disease in a patient, comprising administering to a patient in need of such treatment an effective amount of a compound of claim 1, or a pharmaceutically acceptable salt thereof.

5. A pharmaceutical composition, comprising a compound or a pharmaceutically acceptable salt thereof according to claim 1 with one or more pharmaceutically acceptable carriers, diluents, or excipients.

* * * * *

UNITED STATES PATENT AND TRADEMARK OFFICE
CERTIFICATE OF CORRECTION

| | | |
|---|---|---|
| PATENT NO. | : 8,841,293 B1 | Page 1 of 1 |
| APPLICATION NO. | : 14/195897 | |
| DATED | : September 23, 2014 | |
| INVENTOR(S) | : Steven James Green et al. | |

It is certified that error appears in the above-identified patent and that said Letters Patent is hereby corrected as shown below:

Title Page

Item (72) (Inventors), Line 2, Delete "Zionville," and insert -- Zionsville, --, therefor.

Item (57) (Abstract), Line 3 (Approx), Above "wherein" delete "Formula I".

Signed and Sealed this
Tenth Day of February, 2015

Michelle K. Lee
*Deputy Director of the United States Patent and Trademark Office*